US011612498B2

(12) United States Patent
Hessler et al.

(10) Patent No.: US 11,612,498 B2
(45) Date of Patent: Mar. 28, 2023

(54) EXPANDABLE FUSION DEVICE AND METHOD OF INSTALLATION THEREOF

(71) Applicant: GLOBUS MEDICAL, INC., Audubon, PA (US)

(72) Inventors: Tyler Hessler, Phoenixville, PA (US); Chad Glerum, Pennsburg, PA (US); Adam Friedrich, Cinnaminson, NJ (US); Alex Burkhardt, Akron, PA (US); Jason Zappacosta, Philadelphia, PA (US); Kevin Gahman, Douglassville, PA (US); Matthew Hansell, Schwenksville, PA (US); Andrew Iott, Newtown Square, PA (US); Hilliary Kopp, Virginia Beach, VA (US); Jeff Nichols, Media, PA (US); Joel Cryder, Warrington, PA (US); Edward Karpowicz, Sewell, NJ (US); John Matthews, San Diego, CA (US)

(73) Assignee: Globus Medical, Inc., Audubon, PA (US)

( * ) Notice: Subject to any disclaimer, the term of this patent is extended or adjusted under 35 U.S.C. 154(b) by 77 days.

(21) Appl. No.: 16/991,303

(22) Filed: Aug. 12, 2020

(65) Prior Publication Data
US 2020/0368036 A1 Nov. 26, 2020

Related U.S. Application Data

(63) Continuation of application No. 16/043,781, filed on Jul. 24, 2018, now Pat. No. 10,758,371, which is a
(Continued)

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/4425* (2013.01);
(Continued)

(58) Field of Classification Search
CPC .......... A61F 2/44; A61F 2/4455; A61F 2/447; A61F 2/4611; A61F 2002/30537–3054; A61F 2002/30556
See application file for complete search history.

(56) References Cited

U.S. PATENT DOCUMENTS 6,641,614 B1 * 11/2003 Wagner ................ A61F 2/4455
623/17.15
2013/0204371 A1 * 8/2013 McLuen ................ A61F 2/447
623/17.16

(Continued)

*Primary Examiner* — Eduardo C Robert
*Assistant Examiner* — Michelle C Eckman

(57) ABSTRACT

The present invention provides an expandable fusion device capable of being inserted between adjacent vertebrae to facilitate the fusion process. The expandable fusion device may include first and second endplates, a translation member configured to expand an anterior side and/or posterior side of the device, a plurality of joists configured to connect the first and second endplates to the translation member, and first and second actuation members disposed internally to the device such that openings on a back side of the device can be used to expand or compress the anterior side, the posterior side, or both and such openings may also be used to introduce graft material into the device.

20 Claims, 27 Drawing Sheets

Related U.S. Application Data continuation of application No. 15/601,270, filed on May 22, 2017, now Pat. No. 10,052,215, which is a continuation-in-part of application No. 15/196,231, filed on Jun. 29, 2016, now Pat. No. 9,974,662.

(52) U.S. Cl.
CPC ............... *A61F 2002/30387* (2013.01); *A61F 2002/30428* (2013.01); *A61F 2002/30471* (2013.01); *A61F 2002/30525* (2013.01); *A61F 2002/30538* (2013.01); *A61F 2002/30556* (2013.01); *A61F 2002/30579* (2013.01); *A61F 2002/30593* (2013.01); *A61F 2002/30785* (2013.01); *A61F 2002/30904* (2013.01); *A61F 2002/443* (2013.01)

(56) References Cited

U.S. PATENT DOCUMENTS

| | | |
|---|---|---|
| 2014/0039622 A1 | 2/2014 | Glerum et al. |
| 2014/0067071 A1* | 3/2014 | Weiman ................ A61F 2/4611 623/17.16 |
| 2015/0073552 A1* | 3/2015 | To ......................... A61F 2/4684 623/17.15 |
| 2017/0209292 A1* | 7/2017 | Forsell .................... A61F 5/003 |
| 2018/0193164 A1* | 7/2018 | Shoshtaev ............... A61F 2/447 |
| 2018/0318101 A1* | 11/2018 | Engstrom ............... A61F 2/442 |
| 2019/0000646 A1* | 1/2019 | Daffinson ............. A61F 2/4611 |

* cited by examiner

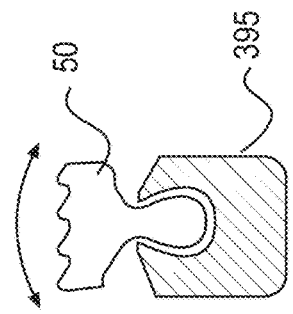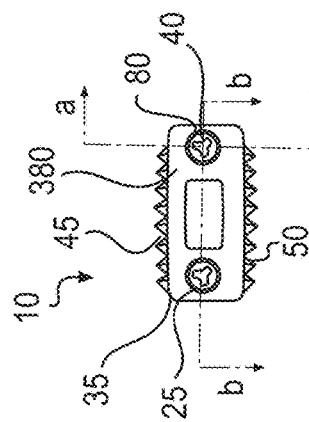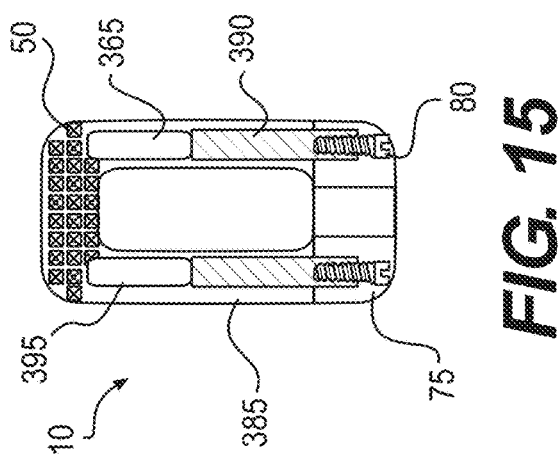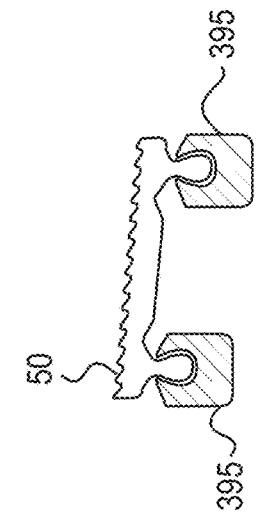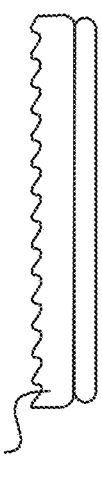

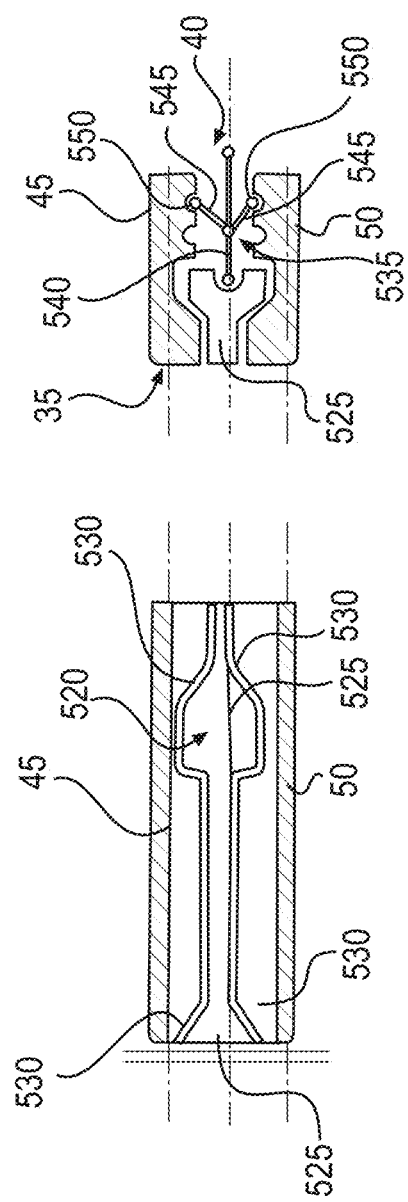

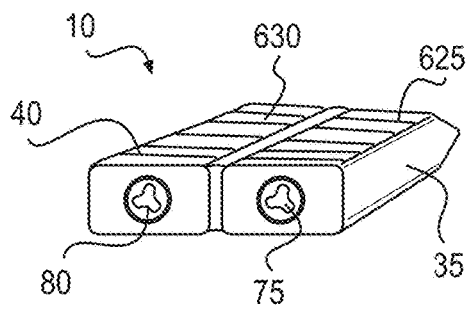
FIG. 40
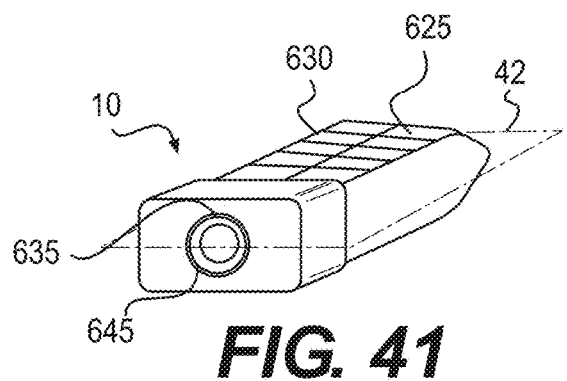
FIG. 41
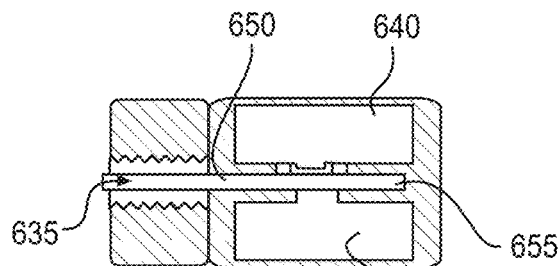
FIG. 42
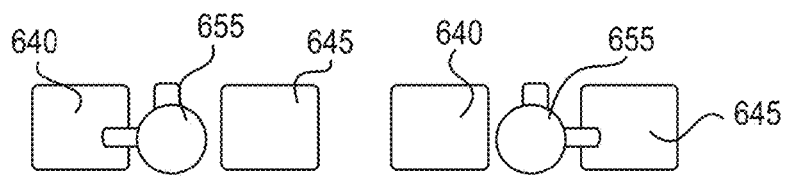
FIG. 43
FIG. 44
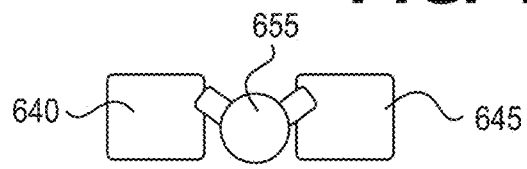
FIG. 45
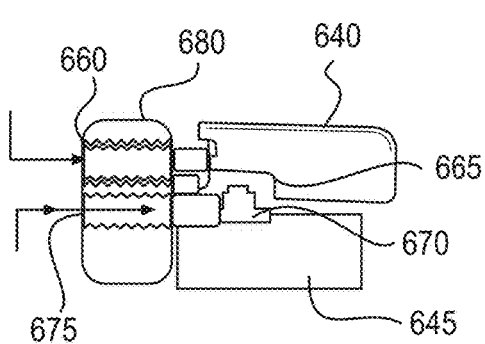
FIG. 46

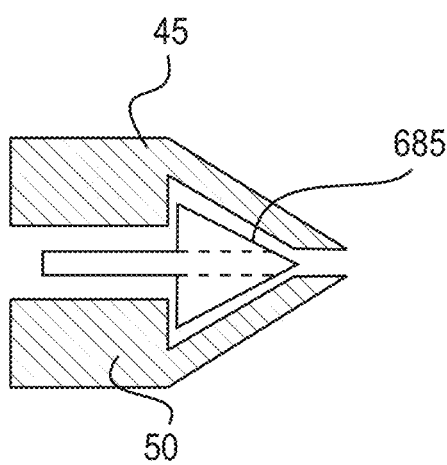
FIG. 47
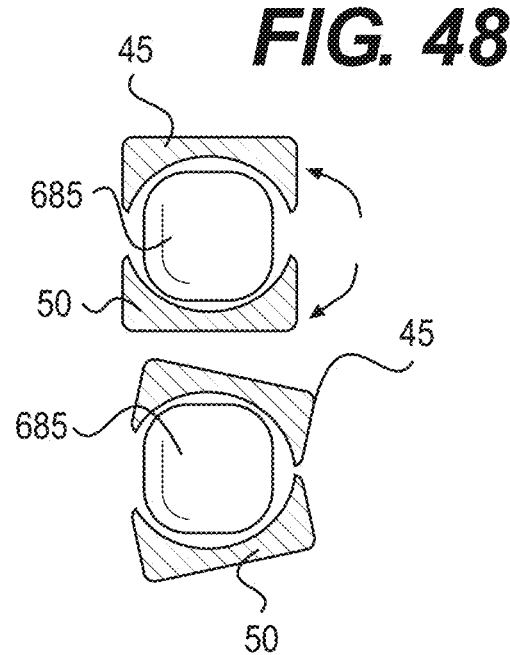
FIG. 48
FIG. 49

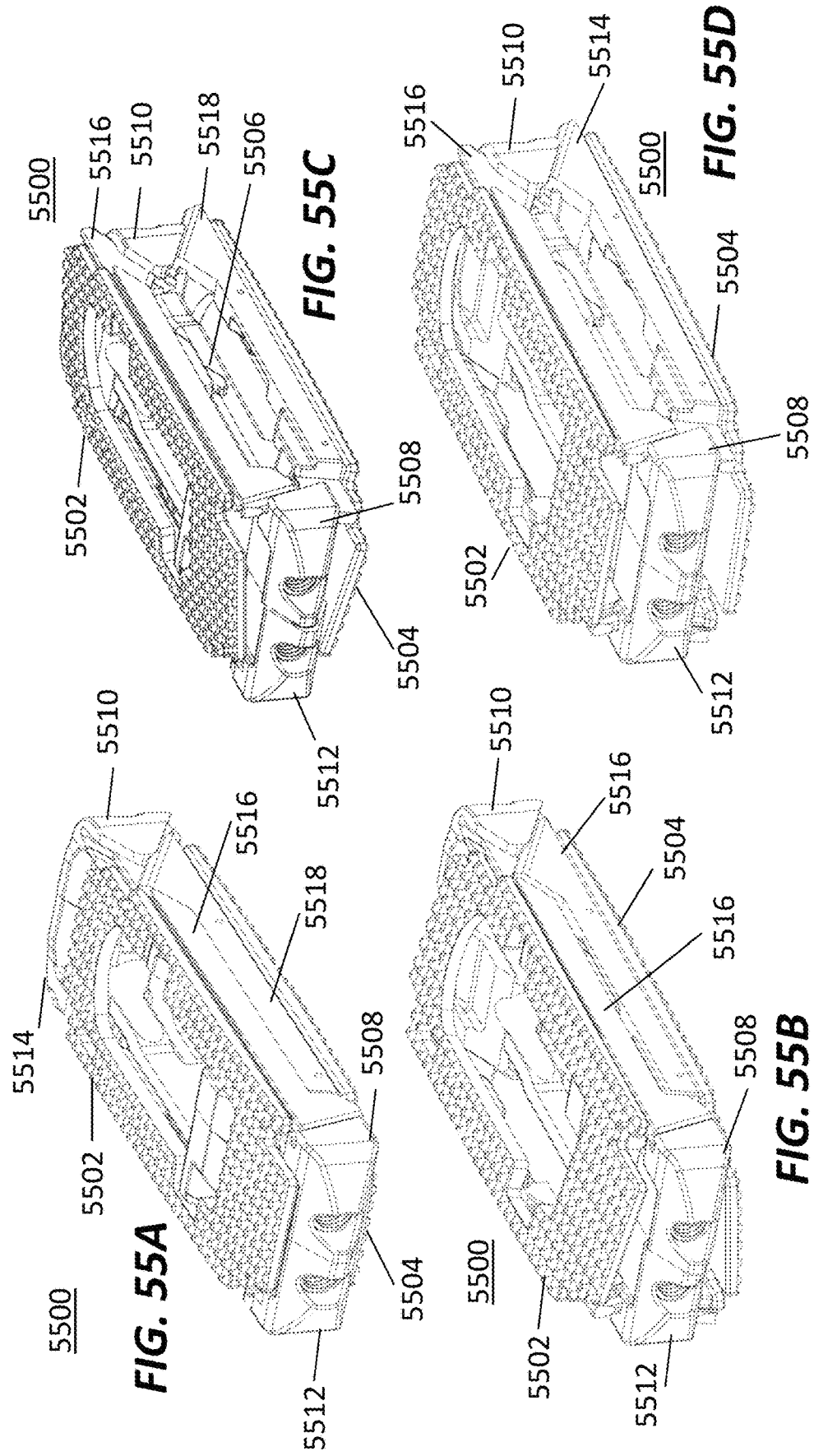

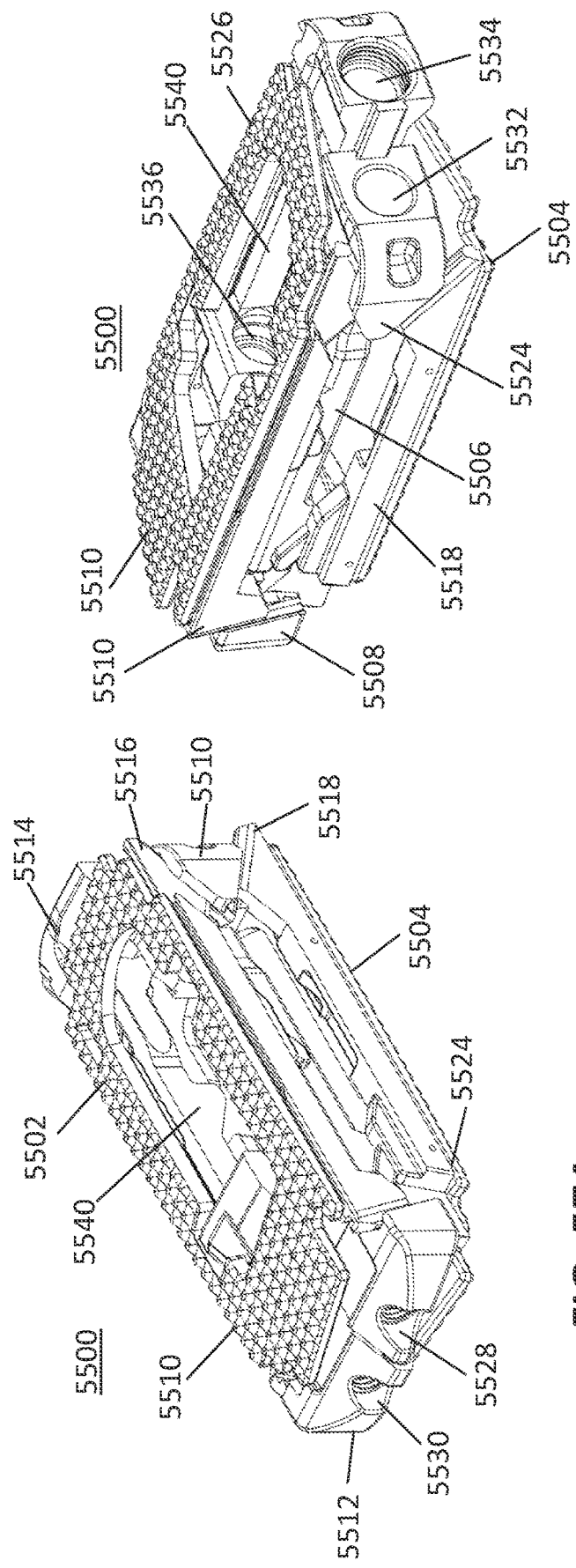

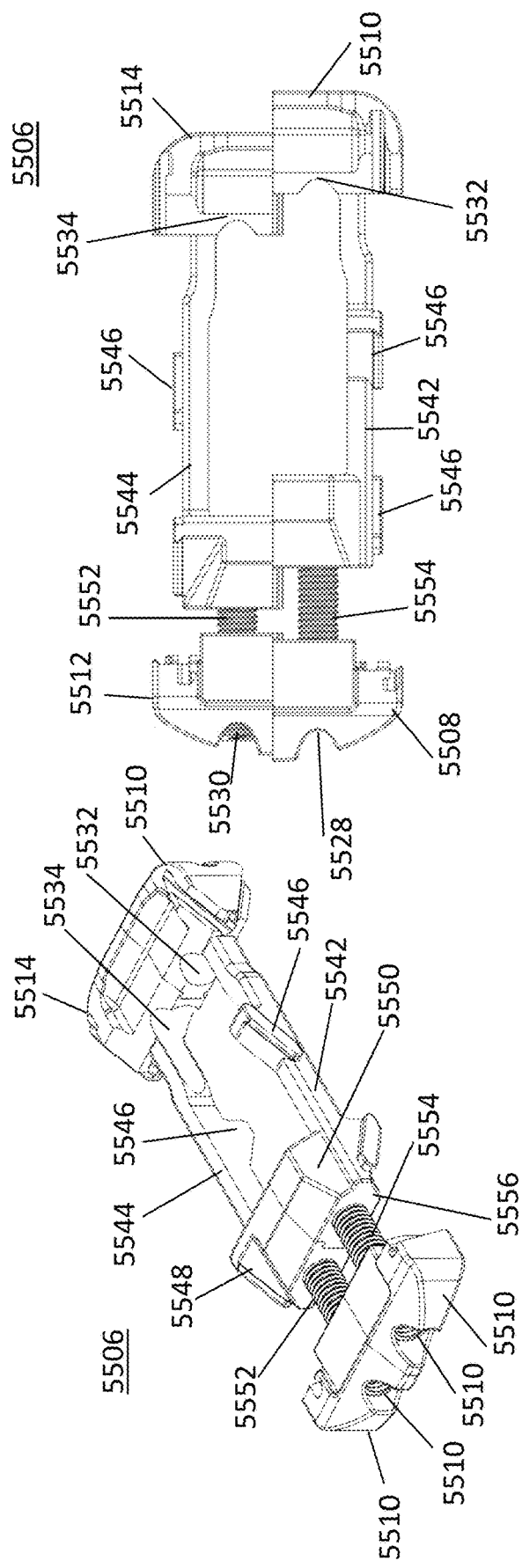

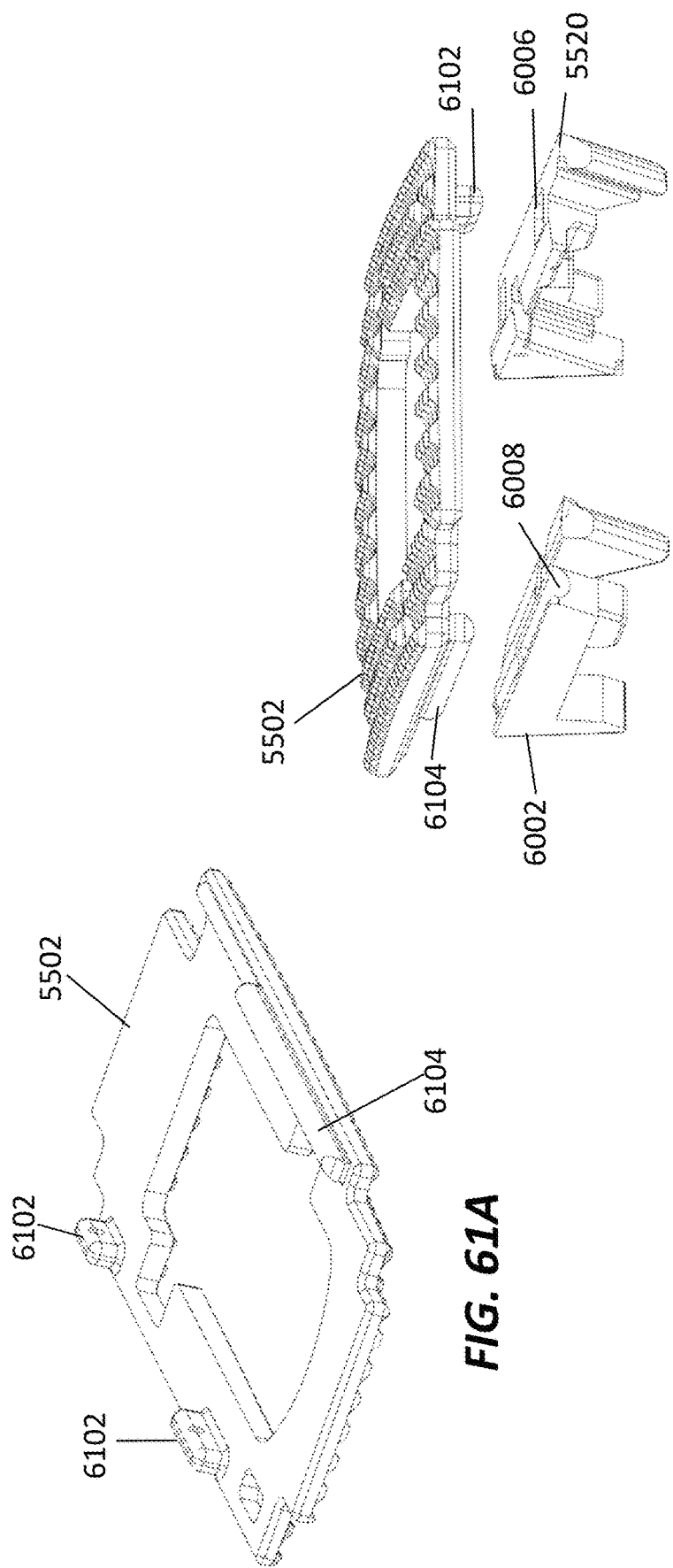

EXPANDABLE FUSION DEVICE AND METHOD OF INSTALLATION THEREOF

CROSS-REFERENCE TO RELATED APPLICATIONS

This application is a continuation of U.S. patent application Ser. No. 16/043,781 filed Jul. 24, 2018 (published as U.S. Pat. Pub. No. 2018-0344474), which is a continuation application of U.S. patent application Ser. No. 15/601,270 filed on May 22, 2017 (now U.S. Pat. No. 10,052,215), which is a continuation-in-part application of U.S. patent application Ser. No. 15/196,231 filed on Jun. 29, 2016 (now U.S. Pat. No. 9,974,662), the contents of which is incorporated by reference herein in its entirety for all purposes.

FIELD OF THE INVENTION

The present invention relates to the apparatus and method for promoting an intervertebral fusion, and more particularly relates to an expandable fusion device capable of being inserted between adjacent vertebrae to facilitate the fusion process.

BACKGROUND

A common procedure for handling pain associated with intervertebral discs that have become degenerated due to various factors such as trauma or aging is the use of intervertebral fusion devices for fusing one or more adjacent vertebral bodies. Generally, to fuse the adjacent vertebral bodies, the intervertebral disc may first be partially or fully removed. Typically, an intervertebral fusion device may then be inserted between neighboring vertebrae to maintain normal disc spacing and restore spinal stability, thereby facilitating an intervertebral fusion.

There are a number of known conventional fusion devices and methodologies in the art for accomplishing the intervertebral fusion. These include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together, alleviating the associated pain.

However, there are drawbacks associated with the known conventional fusion devices and methodologies. For example, two important factors in intervertebral fusion may be the anterior (lordotic) angle adjustment and posterior height adjustment. The lordotic angle may be important in restoring sagittal balance while the posterior height may aid in restoring disc height and indirect decompression of the neural foramen. While convention fusion devices may allow for in-situ expansion, they do not allow for the lordotic angle and posterior height to be adjusted in-situ independently of one another.

SUMMARY

In an exemplary embodiment, the present disclosure provides an expandable fusion device comprising a first endplate, a second endplate, a first joist and a second joist connected to the first endplate, a third joist and a fourth joist connected to the second endplate, a translation member in engagement with the first joist, second joist, third joist, and fourth joist, and a first actuation member in engagement with the translation member assembly. The first actuation member may be configured to move the first joist and the third joist such that the first endplate and the second endplate move in a direction away from the translation member on a first side of the expandable fusion device. The expandable fusion device may also include a second actuation member in engagement with the translation member assembly, wherein the second actuation member is configured to move the second joist and the fourth joist such that the first endplate and the second endplate move in a direction away from the translation member on a second side of the expandable fusion device.

In an exemplary embodiment, An expandable fusion device comprising a first endplate, a second endplate, a translation member disposed at least partially between the first endplate and the second endplate, wherein the translation member assembly comprises an anterior translation component disposed on an anterior side of the expandable fusion device, the anterior translation portion comprises an anterior bore. The expandable fusion device may also include a posterior translation component disposed on a posterior side of the expandable fusion device, wherein the posterior translation portion comprises a posterior bore. The translation member may be configured to expand the fusion device on an anterior side by moving an anterior side of the first endplate and an anterior side of the second endplate and the translation member may be configured to expand the fusion device on a posterior side by moving a posterior side of the first endplate and a posterior side of the second endplate. The first endplate may be engaged with the translation member via a first joist and a second joist, and wherein the second endplate is engaged with the translation member via a third joist and a fourth joist.

BRIEF DESCRIPTION OF THE DRAWINGS

The present invention will become more fully understood from the detailed description and the accompanying drawings, wherein:

FIG. 13 illustrates an expandable fusion device according to another embodiment of the present disclosure.

FIG. 14 is a cross-sectional view of the expandable fusion device of FIG. 13 taken along line a-a.

FIG. 15 is a cross-sectional view of the expandable fusion device of FIG. 13 taken along line b-b FIGS. 16A and 16B are end views of an embodiment of an endplate of the expandable fusion device of FIG. 13 showing a pivot point.

FIG. 17 is a close-up view of an embodiment the endplate of FIGS. 16A and 16B taken along circle 17.

FIG. 18 is a side view of an embodiment of the endplate of FIG. 16 showing contact with a ramped translation member.

FIGS. 34 and 35 illustrate another technique for expansion of an expandable fusion device according to the present disclosure.

FIG. 40 illustrates a perspective view an expandable fusion device according to another embodiment of the present disclosure.

FIG. 41 illustrates a perspective view an expandable fusion device according to another embodiment of the present disclosure.

FIG. 42 is a cross-sectional view of an embodiment of the expandable fusion device of FIG. 41 taken along plane 42.

FIGS. 43-45 illustrate embodiments for expansion of the expandable fusion device of FIG. 41.

FIG. 46 is a cross-sectional view of an expandable fusion device according to another embodiment of the present disclosure.

FIGS. 47-49 illustrate another technique for expansion of an expandable fusion device according to the present disclosure.

FIGS. 55A-55D illustrate perspective views of an exemplary expandable fusion device in various states of expansion according to an embodiment of the present disclosure.

FIGS. 56A-56D illustrate an end view of an exemplary expandable fusion device in various states of expansion according to an embodiment of the present disclosure.

FIGS. 57A and 57B illustrate perspective view of an exemplary expandable fusion device in a state of expansion according to an embodiment of the present disclosure.

FIGS. 58A and 58B illustrate perspective views of an exemplary translation member for an expandable fusion device according to an embodiment of the present disclosure.

FIG. 61A illustrates perspective views of an exemplary endplate for an expandable fusion device according to an embodiment of the present disclosure.

FIG. 61B illustrates a perspective view of an exemplary endplate and exemplary joists for an expandable fusion device according to an embodiment of the present disclosure.

DETAILED DESCRIPTION

Figure 1:
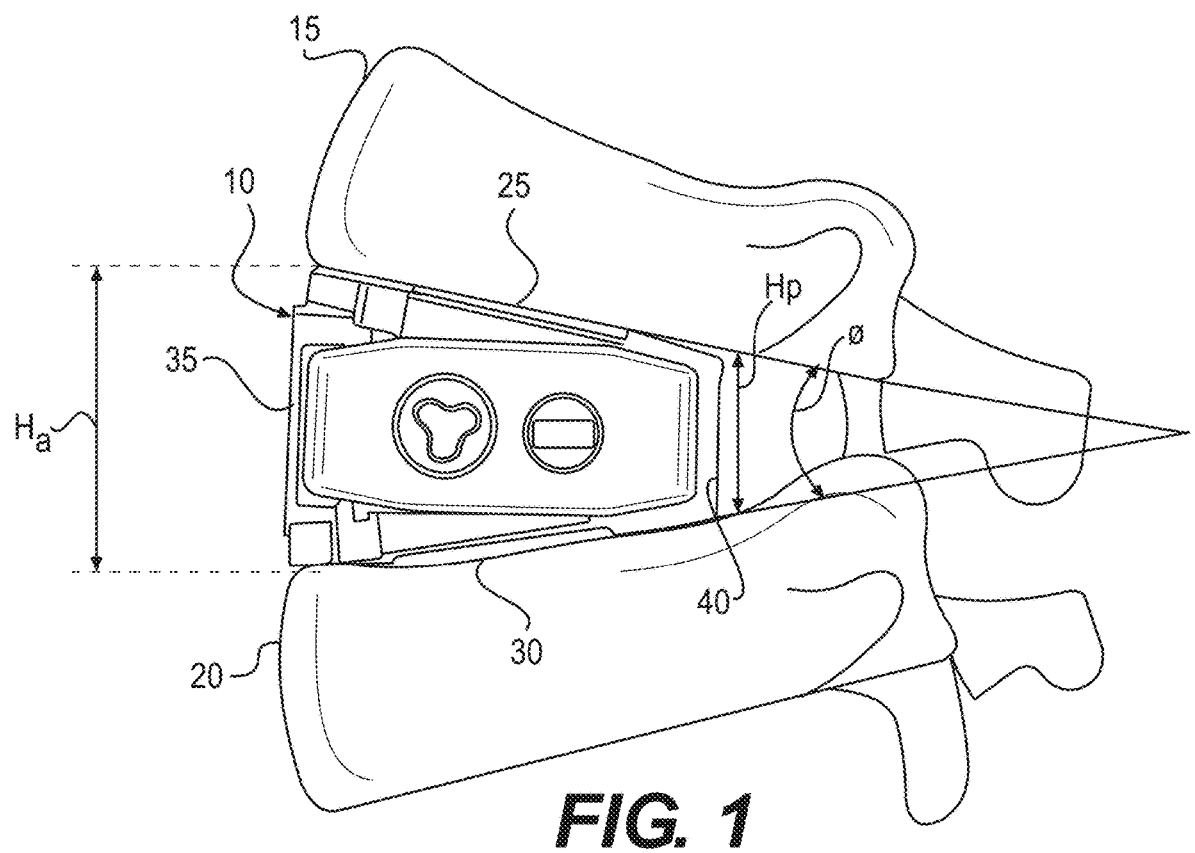
FIG. 1 is a side view of an embodiment of an expandable fusion device shown between adjacent vertebrae according to the present disclosure.

The following description of certain embodiment(s) is merely exemplary in nature and is in no way intended to limit the invention, its application, or uses.

A spinal fusion is typically employed to eliminate pain caused by the motion of degenerated disk material. Upon successful fusion, a fusion device becomes permanently fixed within the intervertebral disc space. Looking at FIG. 1, an exemplary embodiment of an expandable fusion device 10 is shown between adjacent vertebral bodies 15 and 20. The expandable fusion device 10 may be implanted between two adjacent vertebral bodies 15 and 20 in any section of the spine, including the cervical, thoracic, lumbar, and sacral vertebral sections. More than one expandable fusion device 10 may be implanted within the body, for example, between successive or separated vertebrae. As illustrated, the expandable fusion device 10 engages the endplates 25 and 30 of the adjacent vertebral bodies 15 and 20 and, in the installed position, maintains normal intervertebral disc spacing and restores spinal stability, thereby facilitating an intervertebral fusion. The expandable fusion device 10 can be manufactured from a number of materials including titanium, stainless steel, titanium alloys, non-titanium metallic alloys, polymeric materials, plastics, plastic composites, PEEK, ceramic, and elastic materials. In an embodiment, the expandable fusion device 10 can be configured to be placed down an endoscopic tube and into the disc space between the adjacent vertebral bodies 15 and 20.

As illustrated, the expandable fusion device 10 may have an anterior side 35 and a posterior side 40. As will be discussed in more detail below, expansion of the expandable fusion device 10 may be controlled so that the anterior height $H_a$ and the posterior height $H_p$ may be independently controlled. By way of example, the expandable fusion device 10 may have independent anterior expansion and posterior expansion mechanisms. By separate control of anterior expansion and posterior expansion, an operator may adjust the expandable fusion device 10 to provide a desired amount of posterior height $H_p$ and lordotic angle θ. Those of ordinary skill in the art will appreciate that the lordotic angle θ is dependent on the anterior height $H_a$ and posterior height $H_p$ of the expandable fusion device 10. In some embodiments, expansion on the anterior side 35 and the posterior side 40 may also be performed simultaneously to maintain a lordotic angle θ with only changing the anterior height $H_a$ and the posterior height $H_p$ at the same rate. While the expandable fusion device 10 is described herein using several varying embodiments, the expandable fusion device 10 should not be limited to these embodiments.

In some embodiments, the expandable fusion device 10 may be configured and sized to be placed down an insertion tube and into the disc space between the adjacent vertebral bodies 15 and 20. For example, expandable fusion device 10 may be configured for insertion through an insertion tube, such as, e.g., a cannula. It should be noted, however, that the insertion tube may alternatively have any suitable diameter. In one embodiment, expandable fusion device 10 may be inserted through a cannula having a diameter of about 8.5 mm. In some embodiments, the expandable fusion device 10 may have a width in a range of from about 8 mm to about 26 mm, and a length in a range from about 20 mm to about 65 mm, or may have other suitable dimensions. Expandable fusion device 10 may be inserted into a patient via a direct lateral procedure, although anterior, anterolateral, posterolateral or posterior procedures alternatively may be utilized.

Expandable fusion device 10 may have an anterior height $H_a$ and posterior height $H_p$ that are independently adjustable. In some embodiments, the anterior height $H_a$ and posterior height $H_p$ may each be independently expanded to a height that is equal to or greater than about 150% of their respective initial heights. In one embodiment, the anterior height $H_a$ and posterior height $H_p$ may each be independently expanded to a height that is equal to or greater than about 200% of their respective initial heights, or another suitable percentage of their respective initial height.

In some embodiments, bone graft or similar bone growth inducing material can be introduced around and within the expandable fusion device 10 to further promote and facilitate the intervertebral fusion. The expandable fusion device 10, in one embodiment, may be packed with bone graft or similar bone growth inducing material to promote the growth of bone through and around the expandable fusion device 10. Such bone graft may be packed between the endplates of the adjacent vertebral bodies 15 and 20 prior to, subsequent to, or during implantation of the expandable fusion device 10.

In some embodiments, the expandable fusion device 10 may be treated with a titanium and/or hydroxyapatite plasma spray coating to encourage bony on-growth, improving the strength and stability of the connection between the respective component and the underlying bone (e.g., a vertebral body). Any other suitable coating also may be provided on expandable fusion device 10. Such coatings may include therapeutic agents, if desired. Expandable fusion device 10 also may include radiopaque markings to facilitate in vivo visualization. In some embodiments, portions of expandable fusion device 10 may be formed of a radiolucent material, while other portions of expandable fusion device 10 may be formed of radiopaque materials to facilitate imaging of the radiopaque portions of expandable fusion device 10, such as, e.g., actuating mechanisms, endplates, ramps, or the like.

Figure 2:
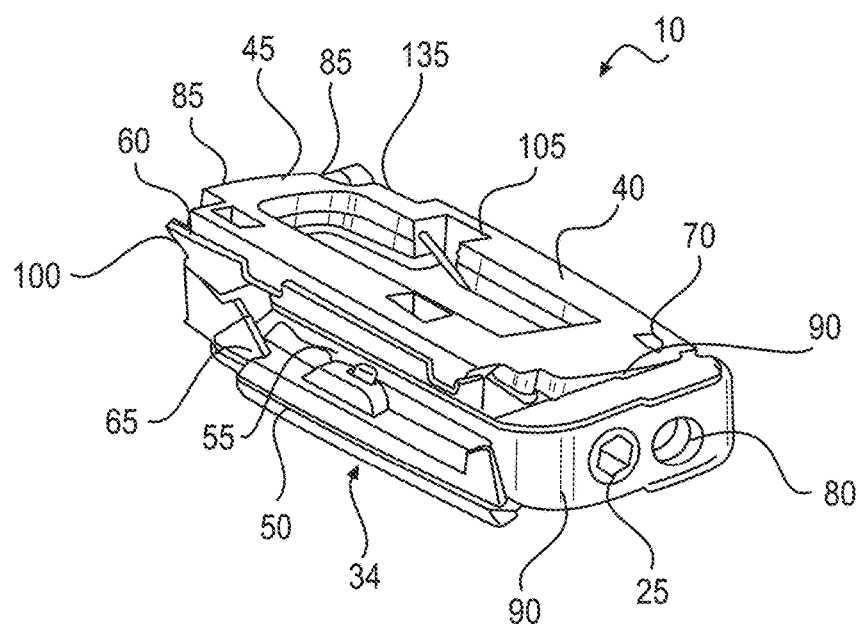
FIG. 2 is a perspective view of an embodiment of an expandable fusion device according to the present disclosure.
Figure 3:
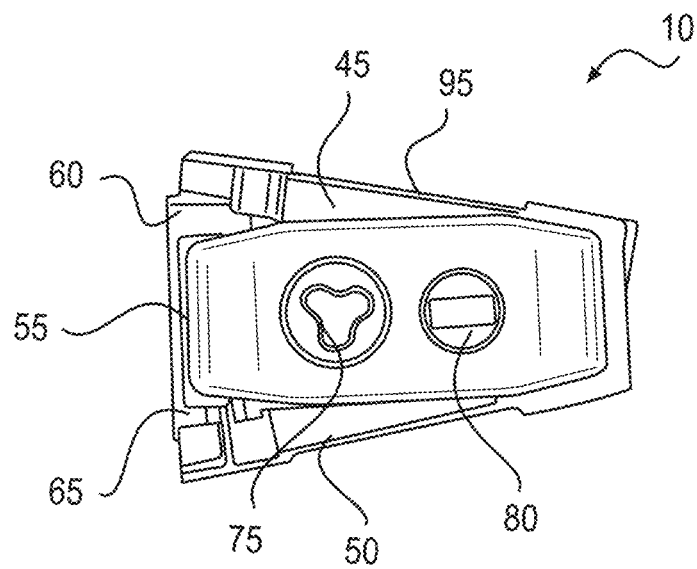
FIG. 3 is an end view of an embodiment of the expandable fusion device of FIG. 2.

With reference now to FIGS. 2 and 3, an embodiment of the expandable fusion device 10 is shown. In an exemplary embodiment, the expandable fusion device 10 includes a first endplate 45, a second endplate 50, and a translation member assembly 55, The expandable fusion device 10 may also include a plurality of ramp frames that transfer motion of the translation member assembly 55 to the first endplate 45 and second endplate 50. In the illustrated embodiment, the expandable fusion device 10 may comprise a first anterior ramp frame 60 for engaging the first endplate 45 on anterior side 35. The expandable fusion device 10 may also comprise a second anterior ramp frame 65 for engaging the second endplate 50 on anterior side 35. The expandable fusion device 10 may also comprise a first posterior ramp frame 70 for engaging the first endplate on posterior side 40. The expandable fusion device 10 may also comprise a second posterior ramp frame (not shown) for engaging the second endplate 50 on posterior side 40. The expandable fusion device 10 may also comprise an actuation member, such as first actuation screw 75, for controlling anterior height $H_a$ and a second actuation member, such as second actuation screw 80, for controlling posterior height $H_p$. It should be recognized that terms anterior and posterior are used to represent anatomical locations with respect to a patient. Accordingly, the terms anterior and posterior when used with respect to the expandable fusion device 10 should not be limited to the specific side shown, as the directions anterior and posterior may change depending, for example, on the direction of insertion.

Expandable fusion device 10 may form a distal end 85 which may be inserted first into the patient's body, and which may be tapered to facilitate insertion between adjacent vertebral bodies 15 and 20. Expandable fusion device 10 may also form a proximal end 90 to which an insertion device (not shown) may be connected. Expandable fusion device 10 may be inserted in a collapsed configuration that is smaller than an expanded configuration. In the expanded configuration, the anterior height $H_a$ and/or posterior height $H_p$ has been increased. Expandable fusion device 10 may be moveable from the collapsed configuration to the expanded configuration.

Figure 4:
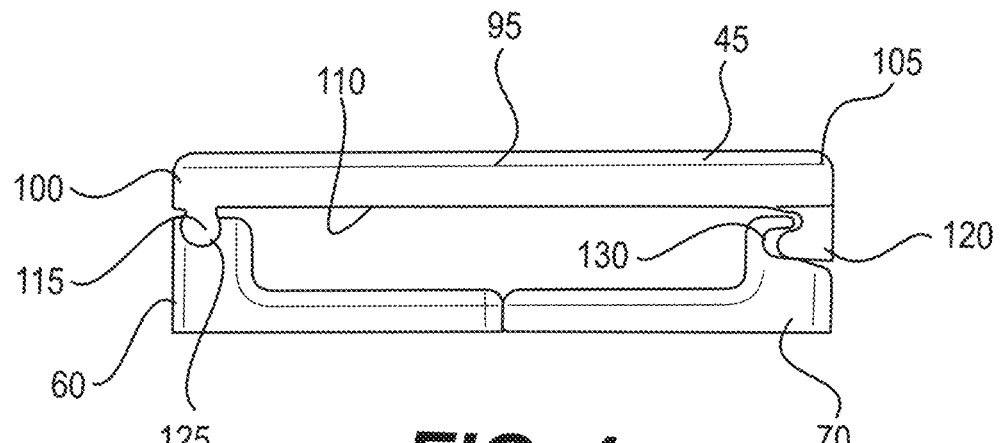
FIG. 4 is end view of an embodiment of an endplate of the expandable fusion device of FIG. 2 showing a pivot point.
Figure 5:
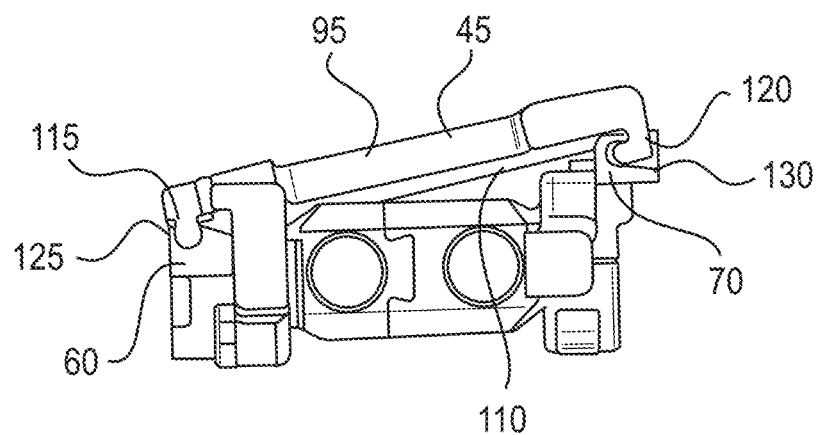
FIG. 5 is another end view of an embodiment of an endplate of the expandable fusion device of FIG. 2 showing a pivot point.

With additional reference to FIGS. 4 and 5, the first endplate 45 will now be described in more detail. Although the following discussion relates to the first endplate 45, it should be understood that it also equally applies to the second endplate 50 as the second endplate 50 is substantially identical to the first endplate 45 in embodiments of the present invention. In the illustrated embodiment, first endplate 45 may comprise an outer surface 95 extending from distal end 85 to proximal end 90. While not illustrated, in an exemplary embodiment, the outer surface 95 may include texturing to aid in gripping the adjacent vertebral bodies. Although not limited to the following, the texturing can include teeth, ridges, friction increasing elements, keels, or gripping or purchasing projections. First endplate 45 may also comprise an anterior endplate side 100 and a posterior endplate side 105. Anterior endplate side 100 may be disposed at anterior side 35 of expandable fusion device 10. Posterior endplate side 105 may be disposed at posterior side 40 of expandable fusion device 10. As best seen on FIG. 4, first endplate 45 may also comprise an inner surface 110.

First endplate 45 may engage first anterior ramp frame 60 and first posterior ramp frame 70. First endplate 45 may include a first mating feature 115 and a second mating feature 120. The first mating feature 115 and second mating feature 120 First mating feature 115 and second mating feature 120 may form joints with corresponding mating features 125 and 130 of the first anterior ramp frame 60 and the first posterior ramp frame 70. The joints formed by engagement of first mating feature 115 and second mating feature 120 with corresponding mating features 125 and 130 may form pivot points to facilitate independent expansion of anterior side 35 and posterior side 40. First mating feature 115 and second mating feature 120 may be balls, tongue or otherwise formed protrusions to allow pivoting of first endplate 45 with respect to first anterior ramp frame 60 and first posterior ramp frame 70. For example, first mating feature 115 may pivot in corresponding mating feature 125 of first anterior ramp frame 60. First mating feature 115 and second mating feature 120 may also allow sliding of first endplate 45 with respect to first anterior ramp frame 60 and/or first posterior ramp frame 70. For example, second mating feature 120 may be pivot and slide in corresponding mating feature 130 of first posterior ramp frame 70. In the illustrated embodiment, the first mating feature 115 and second mating feature 120 may be in the form of a ball, tongue, or other protrusion that mates with corresponding mating features 125 and 130, which may be in the form of a recess, groove, or otherwise formed opening.

In some embodiments, the first endplate 45 and second endplate 50 may further comprise through openings 135. Through opening 135 is shown in first endplate 45 on FIG. 2. The through openings 135 may form an opening that extends from outer surface 95 to inner surface 110. The through openings 135, in an exemplary embodiment, may be sized to receive bone graft or similar bone growth inducing material and further allow the bone graft or similar bone growth inducing material to be packed in a central opening (not shown) of the expandable fusion device 10.

Figure 6:
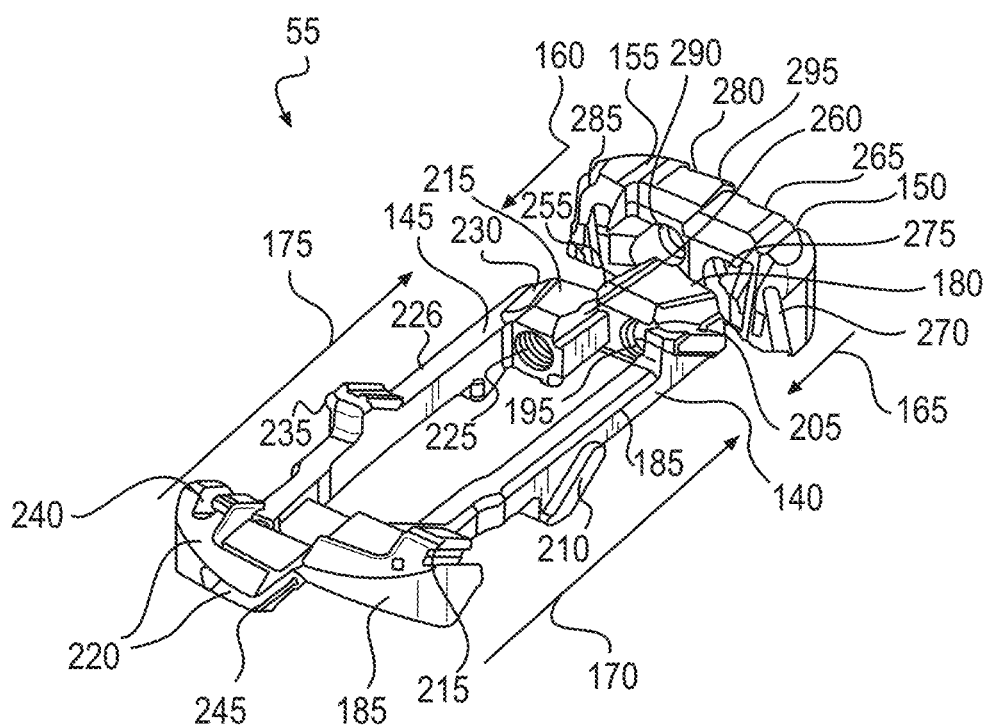
FIG. 6 is a perspective view of an embodiment of a translation member assembly of the expandable fusion device of FIG. 2.
Figure 7:
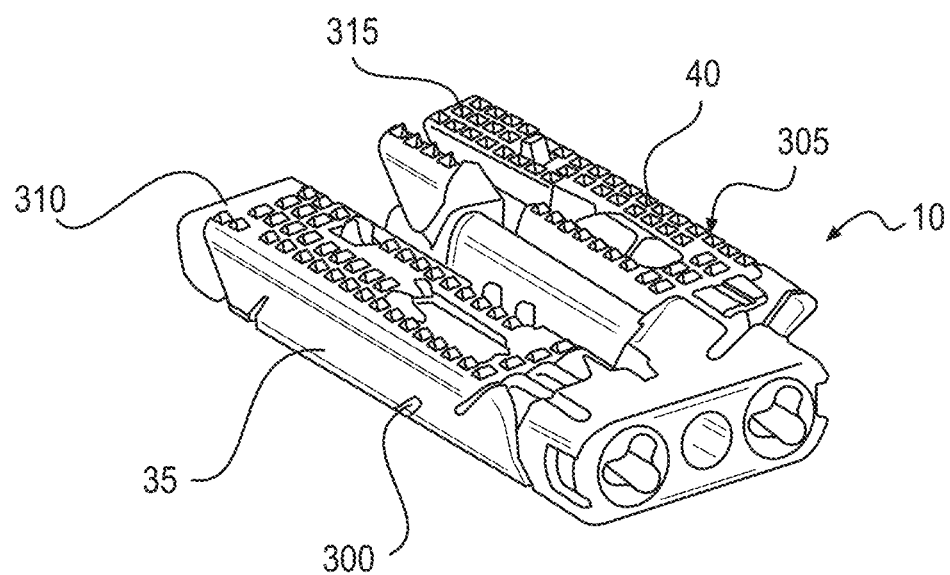
FIG. 7 is a perspective view of an expansion fusion device according to another embodiment of the present disclosure.
Figure 8:
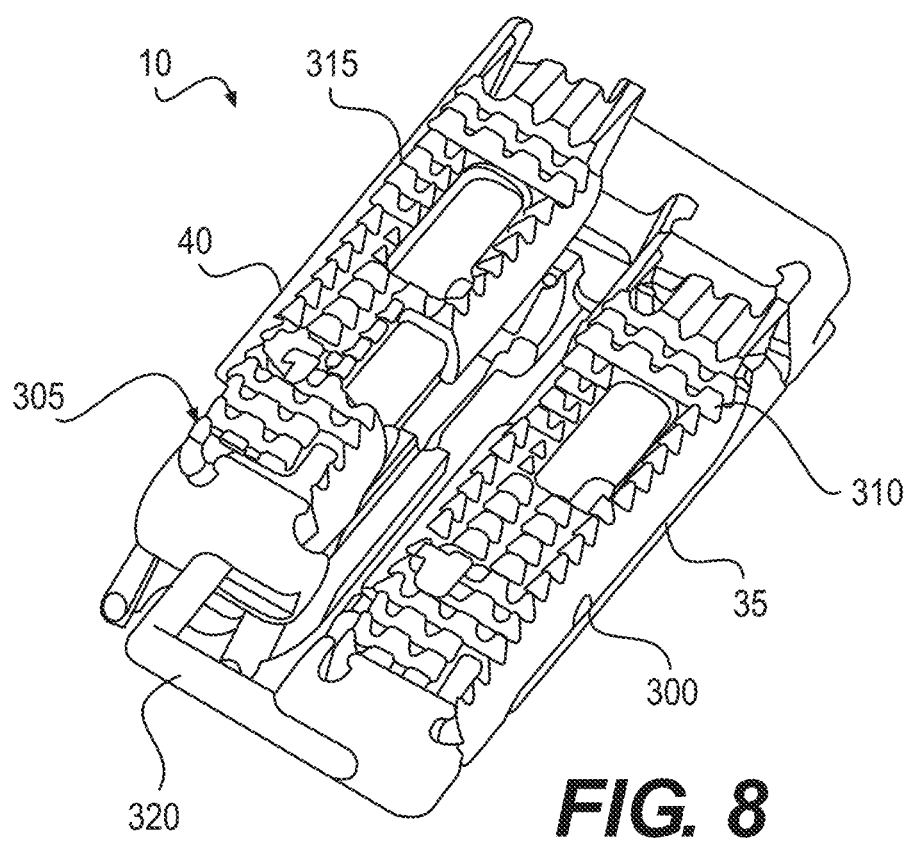
FIG. 8 is another view of an embodiment of the expandable fusion device of FIG. 7.

Turning now to FIG. 6, translation member assembly 55 will now be described in more detail. In the illustrated embodiment, translation member assembly 55 may comprise an anterior translation portion 140, a posterior translation portion 145, an anterior ramped end 150, and a posterior ramped end 155. The anterior translation portion 140 and anterior ramped end 150 may be disposed on anterior side 35 of expandable fusion device 10. The posterior translation portion 145 and posterior ramped end 155 may be disposed on posterior side 40 of expandable fusion device 10. Anterior ramped end 150 and posterior ramped end 155 may be disposed on proximal end 90 of the expandable fusion device 10. Anterior ramped end 150 and posterior ramped end 155 may moveable in the direction indicated by arrows 160 and 165. The anterior translation portion 140 and posterior translation portion 145 may be moveable in the direction indicated by arrows 170 and 175. The anterior translation portion 140, posterior translation portion 145, anterior ramped end 150, and posterior ramped end 155 may engage the corresponding ramp frame to cause expansion of the expandable fusion device. For example, anterior translation portion 140 and anterior ramped end 150 may be moveable to engage first anterior ramp frame 60 and second anterior ramp frame 65, thus casing first anterior ramp frame 60 to push outwardly on first endplate 45 and second anterior ramp frame 65 to push outwardly on second endplate 50. In this manner, anterior side 35 of expandable fusion device may be expanded/contracted by engagement of anterior translation portion 140 and anterior ramped end 150 with first anterior ramp frame 60 and second anterior ramp frame 65. By way of further example, posterior translation portion 145 and posterior ramped end 155 may be moveable to engage first posterior ramp frame 70 and second posterior ramp frame, thus casing first posterior ramp frame 70 to push outwardly on first endplate 45 and second posterior ramp frame to push outwardly on second endplate 50. In this manner, posterior side 40 of expandable fusion device may be expanded/contracted by engagement of posterior translation portion 145 and posterior ramped end 155 with first posterior ramp frame 70 and second anterior ramp frame.

Anterior translation portion 140 may comprise a first end 180 and a second end 185. As illustrated, a connecting bar 190 may extend from first end 180 to second end 185. First end 180 may include a bore 195, which may be threaded, for receiving first actuation screw 75. Anterior translation portion 140 may further comprise one or more ramps, such as ramps 200, 205, 210, that are configured to engage first anterior ramp frame 60 and second anterior ramp frame 65 and transfer movement of the anterior translation portion 140 thereto. Ramp 200 may be disposed at first end 180, ramp 205 may be disposed on connecting bar 190, and ramp 210 may be disposed on second end 185.

Posterior translation portion 145 may comprise a first end 215 and a second end 220. As illustrated, a connecting bar 226 may extend from first end 215 to second end 220. First end 215 may include a bore 225, which may be threaded, for receiving second actuation screw 80. Posterior translation portion 145 may further comprise one or more ramps, such as ramps 230, 235, 240 that are configured to engage first posterior ramp frame 70 and second posterior ramp frame and transfer movement of the posterior translation portion 145 thereto. Ramp 230 may be disposed at first end 215, ramp 235 may be disposed on connecting bar 226, and ramp 240 may be disposed on second end 220.

Anterior translation portion 140 may engage posterior translation portion 145. In some embodiments, anterior translation portion 140 may slidingly engage posterior translation portion 145, for example, with a dovetail or other suitable sliding joint. As illustrated, anterior translation portion 140 may comprise a flange 245 or other suitable protrusion at second end 185 that may be received in a slot 250 at second end 220 of posterior translation portion 145. The flange 245 may have an enlarged edge (not shown) to prevent removal of flange 245 from slot. As further illustrated, anterior translation portion 140 may further comprise a protrusion 255 (e.g., tongue) at first end 180. The flange 245 and slot 250 may form a sliding and interlocking joint that allows translation of the anterior translation portion 140 and the posterior translation portion 145 with respect to one another. that may be received in a groove 260 at first end 215 of posterior translation portion 145. The protrusion 255 and groove 260 may form a sliding and interlocking joint that also allows translation of the anterior translation portion 140 and the posterior translation portion 145 with respect to one another.

Anterior ramped end 150 may comprise a body portion 265. Body portion 265 may comprise ramp 270 and bore 275. Ramp 270 may be configured to engage first anterior ramp frame 60 and second anterior ramp frame 65 and transfer movement of the anterior ramped end 150 thereto. Bore 275 may be threaded for receiving first actuation screw 75. Anterior ramped end 150 may be coupled to anterior translation portion 140 via first actuation screw 75.

Posterior ramped end 155 may comprise a body portion 280, which may comprise ramp 285 and bore 290. Ramp 285 may be configured to engage first posterior ramp frame 70 and second anterior ramp frame and transfer movement of the posterior ramped end 155 thereto. Bore 290 may be threaded for receiving second actuation screw 80. Posterior ramped end 155 may be coupled to posterior translation portion 145 via second actuation screw 80. Posterior ramped end 155 may engage anterior ramped end 150, for example, via a sliding connection, such as dovetail connection 295.

Figure 64:
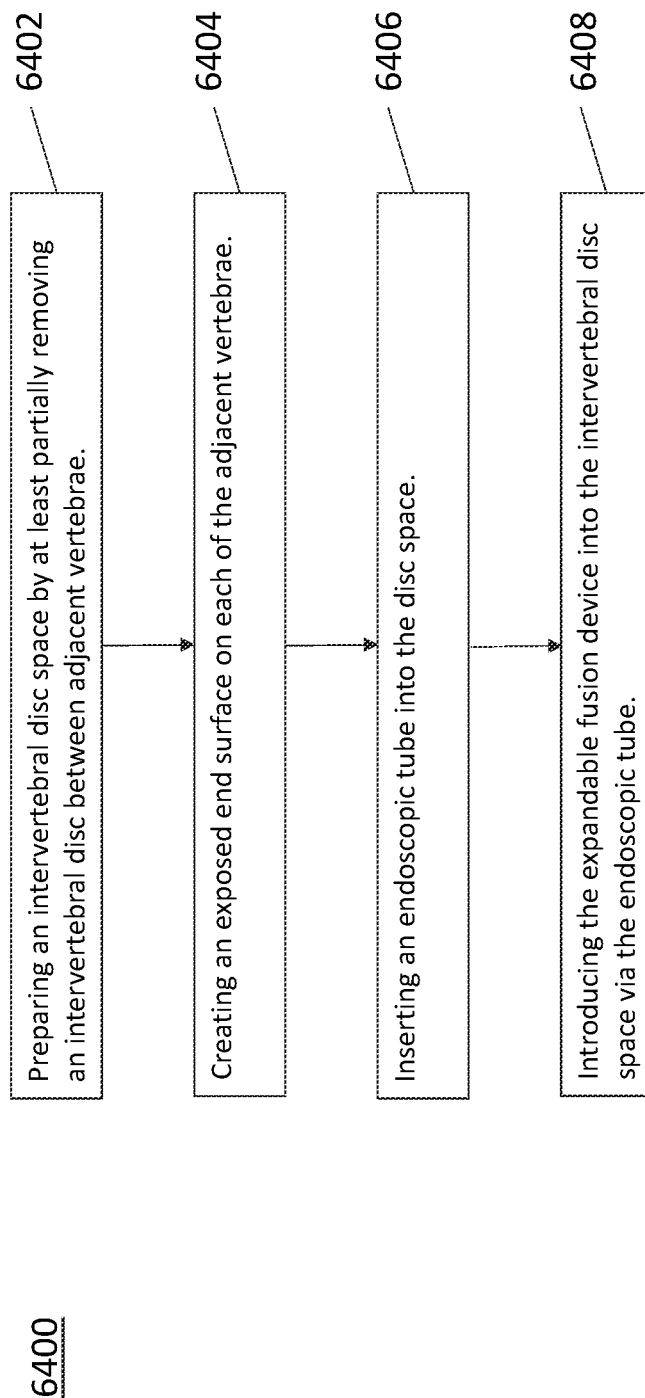
FIG. 64. a method of installing the expandable fusion device 10.

FIG. 64 shows a method 6400 of installing the expandable fusion device 10 of FIGS. 1-6 is now discussed in accordance with exemplary embodiments. Prior to insertion of the expandable fusion device 10, the intervertebral space may be prepared at step 6402. In one method of installation, a discectomy may be performed where the intervertebral disc, in its entirety, is removed. Alternatively, only a portion of the intervertebral disc can be removed. The endplates of the adjacent vertebral bodies 15 and 20 may then be scraped to create an exposed end surface for facilitating bone growth across the intervertebral space at step 6404. One or more endoscopic tubes may then be inserted into the disc space at step 6406. The expandable fusion device 10 may then be introduced into the intervertebral space down an endoscopic tube and seated in an appropriate position in the intervertebral disc space at step 6408.

After the expandable fusion device 10 has been inserted into the appropriate position in the intervertebral disc space, the expandable fusion device 10 can then be expanded into the expanded configuration. As previously described, expansion of the anterior side 35 and posterior side 40 may be independently controlled. For example, the anterior side 35 and posterior side 40 may be separately expanded at different times, expanded at different rates, and/or expanded at the rate (e.g., to maintain a desired lordotic angle θ). To expand the anterior side 35 of the expandable fusion device 10, the anterior ramped end 150 and anterior translation portion 140 may be moved with respect to one another. For example, the anterior ramped end 150 may be moved toward anterior translation portion 140 in direction indicated by arrow 165. By way of further example, anterior translation portion 140 may be moved toward anterior ramped end 150 in direction indicated by arrow 170. Or both the anterior ramped end 150 and anterior translation portion 140 may be moved toward one another. As the anterior ramped end 150 and anterior translation portion 140 move with respect to one another, they push against the corresponding first anterior ramp frame 60 and second anterior ramp frame 65, which in turn push against the first endplate 45 and second endplate 50 to cause an increase in anterior height $H_a$. To expand the posterior side 40 of the expandable fusion device 10, the posterior ramped end 155 and posterior translation portion 145 may be moved with respect to one another. For example, the posterior ramped end 155 may be moved toward posterior translation portion 145 in direction indicated by arrow 160. By way of further example, posterior translation portion 145 may be moved toward posterior ramped end 155 in direction indicated by arrow 175. Or both the posterior ramped end 155 and posterior translation portion 145 may be moved toward one another. As the posterior ramped end 155 and posterior translation portion 145 move with respect to one another, they push against the corresponding first posterior ramp frame 70 and second posterior ramp frame, which in turn push against the first endplate 45 and second endplate 50 to cause an increase in posterior height $H_p$.

In the event the expandable fusion device 10 needs to be repositioned or revised after being installed and expanded, the expandable fusion device 10 can be contracted back to the unexpanded configuration, repositioned, and expanded again once the desired positioning is achieved. To contract the expandable fusion device 10, the above-described procedure may be reversed. By way of example, for contraction of anterior side 35, the anterior ramped end 150 and anterior translation portion 140 may be moved with away from one another using first actuation screw 75. For contraction of posterior side 40, the posterior ramped end 155 and posterior translation portion 145 may be moved with away from one another using second actuation screw 80.

First actuation screw 75 or another other suitable actuation mechanism may be used to facilitate expansion of anterior side 35. As previously described, first actuation screw 75 may be disposed in bore 275 of anterior ramped end 150 and bore 195 of anterior translation portion 140. When first actuation screw 75 is rotated in a first direction, the anterior ramped end 150 and anterior translation portion may be drawn closer together. When first actuation screw 75 is rotated in a second direction (opposite the first direction), the anterior ramped end 150 and anterior translation portion 140 may move away from one another.

Second actuation screw 80 or another other suitable actuation mechanism may be used to facilitate expansion of posterior side 40. As previously described, second actuation screw 80 may be disposed in bore 290 of posterior ramped end 155 and bore 225 of posterior translation portion 145. When second actuation screw 80 is rotated in a first direction, the posterior ramped end 155 and posterior translation portion 145 may be drawn closer together. When second actuation screw 80 is rotated in a second direction (opposite the first direction), the posterior ramped end 155 and posterior translation portion 145 may move away from one another.

With reference now to FIGS. 7-11, an expandable fusion device 10 is shown according to another embodiment. As illustrated, the expandable fusion device 10 may comprise an anterior side 35 and a posterior side 40. In the illustrated embodiment, the expandable fusion device 10 comprises a pair of expandable implants, illustrated as anterior expandable implant 300 and posterior expandable implant 305, respectively. The anterior expandable implant 300 comprise a pair of opposing anterior endplates 310 and the posterior expandable implant 305 comprises a pair of opposing posterior endplates 315. The anterior endplates 310 and the posterior endplates 315 may be expanded independently allowing control of height on each side of expandable fusion device 10. The resultant lordotic angle θ may be based on the difference in height between the anterior expandable implant 300 and the posterior expandable implant 305. The anterior expandable implant 300 may be secured to the posterior expandable implant 305. By way of example, a connecting bar 320 may attach the anterior expandable implant 300 to the posterior expandable implant 305.

Figure 9:
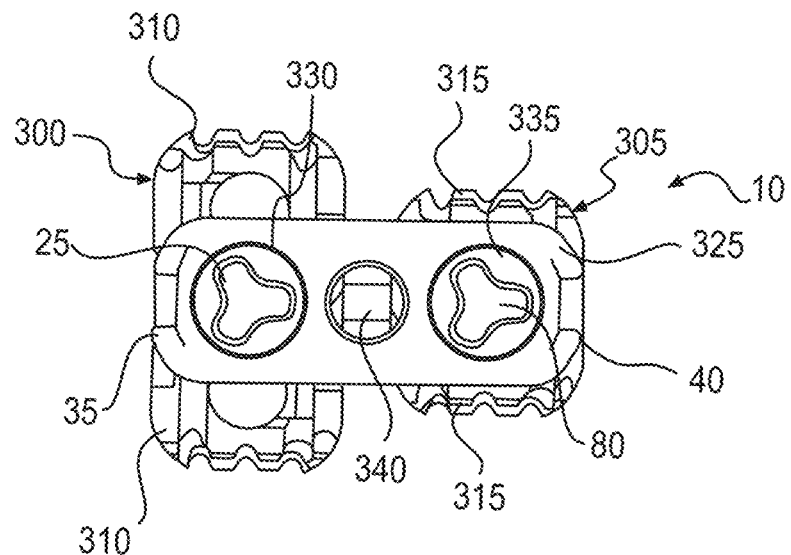
FIG. 9 is an end view of an embodiment of the expandable fusion device of FIG. 7.

FIG. 9 illustrates a front end view of expandable fusion device 10 with anterior endplates 310 expanded. As illustrated, the anterior expandable implant 300 and posterior expandable implant 305 may share a front (or driving) ramp 325. Bores 330 and 335 may be formed in front ramp 325 through which first actuation screw 75 and second actuation screw 80 may be disposed. Anterior expandable implant 300 may be expanded by rotation of first actuation screw 75, and posterior expandable implant 305 may be expanded by rotation of second actuation screw 80. As the first actuation screw 75 rotates, anterior ramps (not shown) may be drawn to front ramp 325, while anterior ramps and front ramp 325 engage anterior endplates 310 causing expansion of anterior expandable implant 300. As the second actuation screw 80 rotates, posterior ramps (not shown) may be drawn to front ramp 325, while posterior ramps and front ramp 325 engage posterior endplates 315 to cause expansion of posterior expandable implant 305. Front ramp 325 may further comprise a graft hole 340. As illustrated, graft hole 340 may be disposed between bores 330 and 335. Graft hole 340 may be sized to receive bone graft or similar bone growth inducing material and further allow the bone graft or similar bone growth inducing material to be packed in a central opening (not shown) of the expandable fusion device 10.

Figure 10:
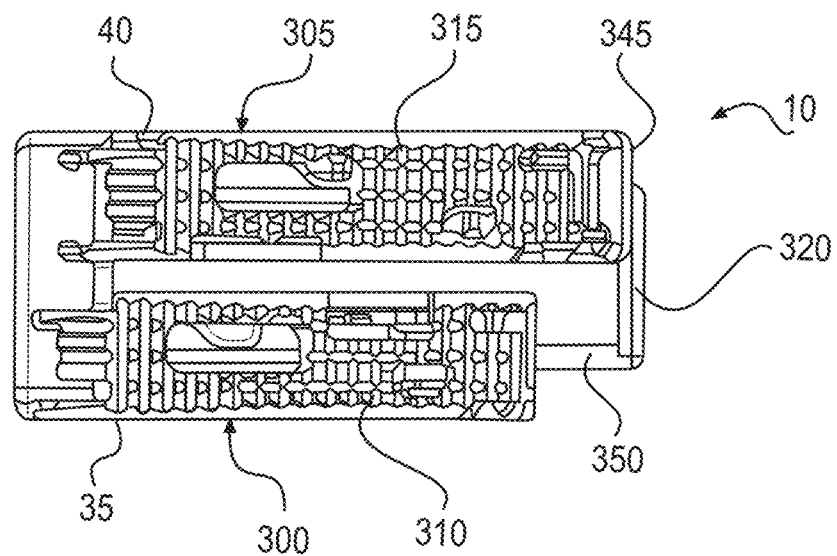
FIG. 10 is a top view of an embodiment of the expandable fusion device of FIG. 7.

FIG. 10 illustrates a top view of expandable fusion device 10 with anterior endplates 310 expanded. As illustrated, connecting bar 320 may secure anterior expandable implant 300 and posterior expandable implant 305. In some embodiments, connecting bar 320 may be rigidly attached to nose 345 of posterior expandable implant 305. The connecting bar 320 may be housed within a center shaft 350 on anterior expandable implant 300 and may translate as anterior expandable implant 300 may be expanded or collapsed.

Any suitable technique may be used for expansion of anterior expandable implant 300 and posterior expandable implant 305. One technique for expansion of anterior expandable implant and posterior expandable implant 305 may be provided in U.S. Patent Publication No. 2014/0067071, the disclosure of which in incorporated herein by reference. While not illustrated, the anterior expandable implant 300 and posterior expandable implant 305 may each comprise a central ramp. The central ramps may include a ramps that engage anterior endplates 310 and the posterior endplates 315. For expansion of anterior side 35, the first actuation screw 75 may be rotated to draw the central ramp of the anterior expandable implant 300 and the front (or driving) ramp 325 closer together, for example, by pulling the central ramp toward the front ramp 325. The central ramp and front ramp 325 may engage the anterior endplates 310 forcing them apart. While not shown the central ramp and front ramp 325 may comprise ramps that engage corresponding ramps in the anterior endplates 310. For expansion of posterior side 40, the second actuation screw 80 may be rotated to draw the central ramp of the posterior expandable implant 305 and the front (or driving) ramp 325 closer together, for example, by pulling the central ramp toward the front ramp 325. The central ramp and front ramp 325 may engage the posterior endplates 315 forcing them apart. While not shown the central ramp and front ramp 325 may comprise ramps that engage corresponding ramps in the posterior endplates 315.

While the preceding description provides discusses techniques to facilitate expansion it should be understood that the present disclosure should not be limited to these techniques. Any suitable technique for facilitating independent expansion of anterior side 35 and posterior side 40 of expandable fusion device 10 may be used. The following description of FIGS. 11-54 provide alternative expansion techniques that may be used to facilitate expansion of an anterior side 35 and posterior side 40 of an expandable fusion device.

Figure 11:
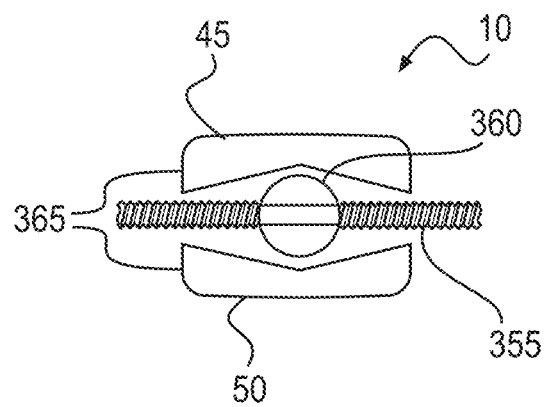
FIG. 11 illustrate an expandable fusion device according to another embodiment of the present disclosure.

Referring now to FIG. 11, expandable fusion device 10 is shown according to another embodiment. In the illustrated embodiment, expandable fusion device 10 comprises first endplate 45 and second endplate 50. As illustrated, the expandable fusion device 10 may further comprise an actuation screw 355 coupled to a ball bearing 360. The actuation screw 355 and ball bearing 360 may be disposed between the first endplate 45 and the second endplate 50. Rotation of actuation screw 355 would in in turn drive ball bearing 360. The ball bearing 360 may be moved back and forth between the first endplate 45 and second endplate 50 to adjust height. The first endplate 45 and second endplate 50 may be coupled to hinges 365. As height of the expandable fusion device 10 may be adjusted, the first endplate 45 and second endplate 50 may pivot at hinges 365. While not shown, the hinges 365 may be fixed to a frame.

Figure 12:
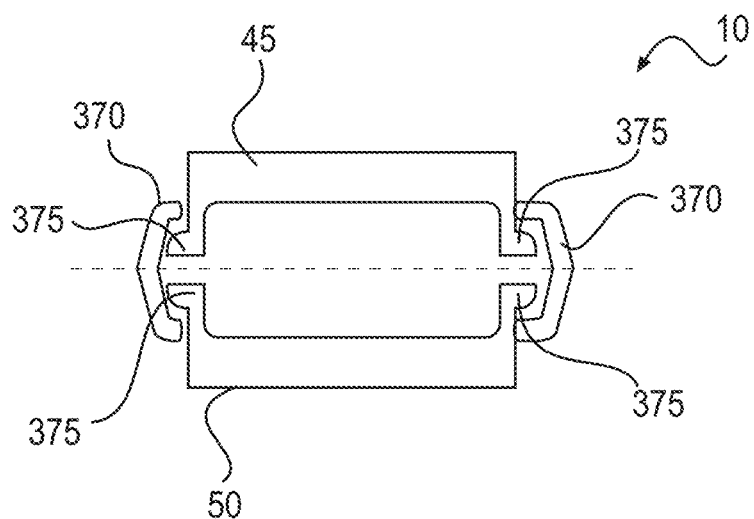
FIG. 12 illustrate an expandable fusion device according to another embodiment of the present disclosure.

FIG. 12 illustrates expandable fusion device 10 according to another embodiment. As illustrated, expandable fusion device 10 may comprise first endplate 45 and second endplate 50. The expandable fusion device 10 may further comprise a frame 370. The frame 370 may have walls that are angled, tapered, or otherwise formed. In the illustrated embodiment, the first endplate 45 and second endplate 50 may each have lips 375 that may overlap frame 370 and thereby prevent the first endplate 45 and second endplate 50 from dislocating. The first endplate 45 and second endplate 50 may move freely within the frame 370, allowing the expandable fusion device 10 to expand or contract while the first endplate 45 and second endplate 50 may conform to anatomy of the adjacent vertebral bodies 15 and 20.

FIGS. 13-15 illustrate expandable fusion device 10 according to another embodiment. FIG. 14 is a cross-sectional view of FIG. 13 taken along line a-a. FIG. 15 is a cross-sectional view of FIG. 13 taken along line b-b. In the illustrated embodiment, expandable fusion device 10 may comprise a first endplate 45 and a second endplate 50. Expandable fusion device 10 may further comprise a rear plate 380 through which a first actuation screw 75 and a second actuation screw 80 may be disposed. First actuation screw 75 may be coupled to a first actuation ramp 385. Second actuation screw 80 may be coupled to a second actuation ramp 390. Ramped portions 395 may also be coupled to the first endplate 45 and second endplate 50. First actuation screw 75 may be rotated to drive first actuation ramp 385 to push ramped portion 395, which in turn may push first endplate 45 to cause it to move outward on anterior side 35. Second actuation screw 80 may be rotated to drive second actuation ramp 390 to push ramped portion 395, which in turn may push first endplate 45 to cause to move outward on posterior side 40. In this manner, expansion on anterior side 35 and posterior side 40 may be independently controlled. FIGS. 16a, 16b, and 17 illustrate the second endplate 50 pivotally attached to ramped portion 395. FIG. 18 illustrates second endplate 50 and ramped portion 395. Ramped portion 395 may be coupled to second endplate 50 to form an endplate assembly.

Figure 19:
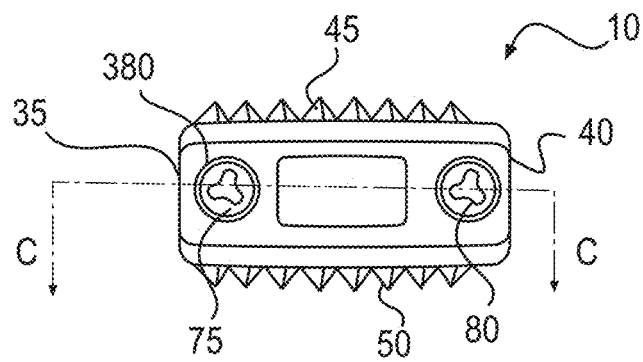
FIG. 19 is an end view of an expandable fusion device according to another embodiment of the present disclosure.
Figure 20:
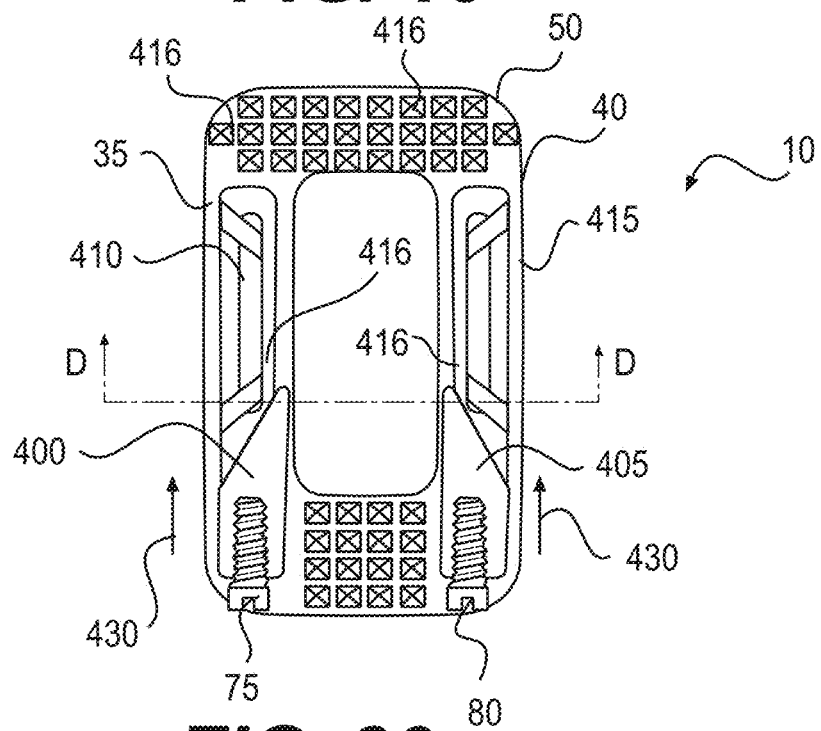
FIG. 20 is a cross-sectional view of the expandable fusion device of FIG. 19 taken along line c-c.
Figure 21:
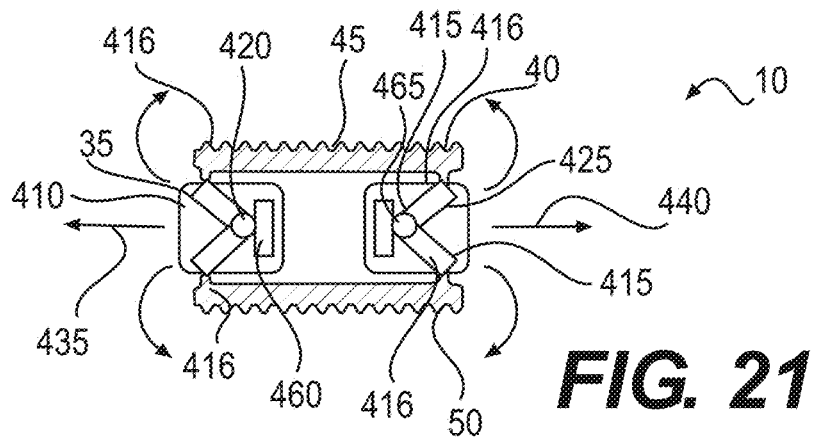
FIG. 21 is a cross-sectional view of the expandable fusion device of FIG. 20 taken along line d-d.

FIGS. 19-21 illustrate expandable fusion device 10 according to another embodiment. FIG. 20 is a cross-sectional view of FIG. 19 taken along line c-c. FIG. 21 is a cross-sectional view of FIG. 20 taken along line d-d. As illustrated, the first actuation screw 75 and second actuation screw 80 may be disposed through rear plate 380. First actuation screw 75 and second actuation screw 80 may engage first shim 400 and second shim 405, respectively. First shim 400 and second shim 405 may engage a first pivot assembly 410 and second pivot assembly 415. First pivot assembly 410 and second pivot assembly 415 may pivot at first pivot point 420 and second pivot point 425, respectively. In the illustrated embodiment, first pivot assembly 410 and second pivot assembly 415 may each comprise pivot arms 416 coupled at first pivot point 420 and second pivot point 425, respectively. First actuation screw 75 may be rotated to cause first shim 400 to move in the direction of arrow 430 on FIG. 20. First shim 400 may engage first pivot assembly 410 pushing it to cause first pivot assembly 410 to move outward in direction indicated by arrow 435. First pivot assembly 410 may lengthen as it moves outward, which in turn pushes on first endplate 45 and second endplate 50 causing them to move away from one another, thus expanding on anterior side 35. Second actuation screw 80 may be rotated to cause second shim 405 to move in the direction of arrow 430 on FIG. 20. Second shim 405 may engage second pivot assembly 415 pushing it to cause second pivot assembly 415 to move outward in the direction of arrow 440. Second pivot assembly 415 may lengthen as it moves outward, which in turn pushes on first endplate 45 and second endplate 50 causing them to move away from one another, thus expanding on posterior side 40.

Figure 22:
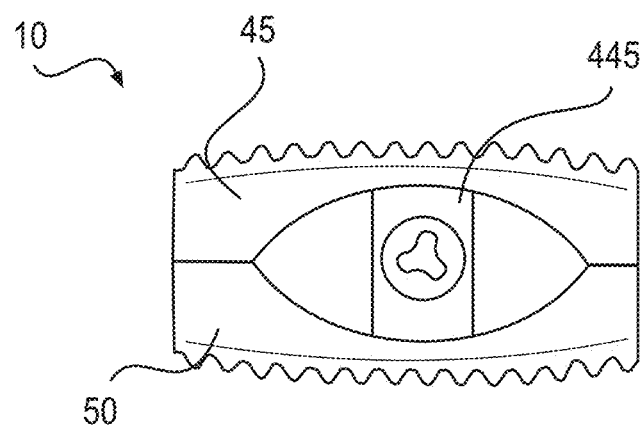
FIGS. 22 and 23 are end views of an expandable fusion device according to another embodiment of the present disclosure.
Figure 23:
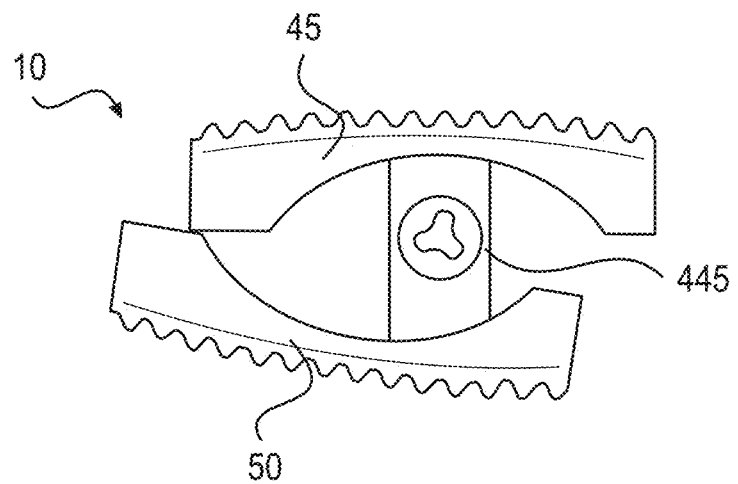

FIGS. 22 and 23 illustrate expandable fusion device 10 according to another embodiment. As illustrated, expandable fusion device 10 may comprise first endplate 45 and second endplate 50. Cam member 450 may be disposed between first endplate 45 and second endplate 50. Cam member 450 may engage first endplate 45 and second endplate 50. Cam member 450 may be rotatable. In some embodiments, cam member 450 may be rotated to adjust the angle between first endplate 45 and second endplate 50. FIG. 23 illustrates expandable fusion device 10 after rotation of cam member 450 to adjust the angle between the first endplate and the second endplate 50 in accordance with present embodiments.

Figure 24:
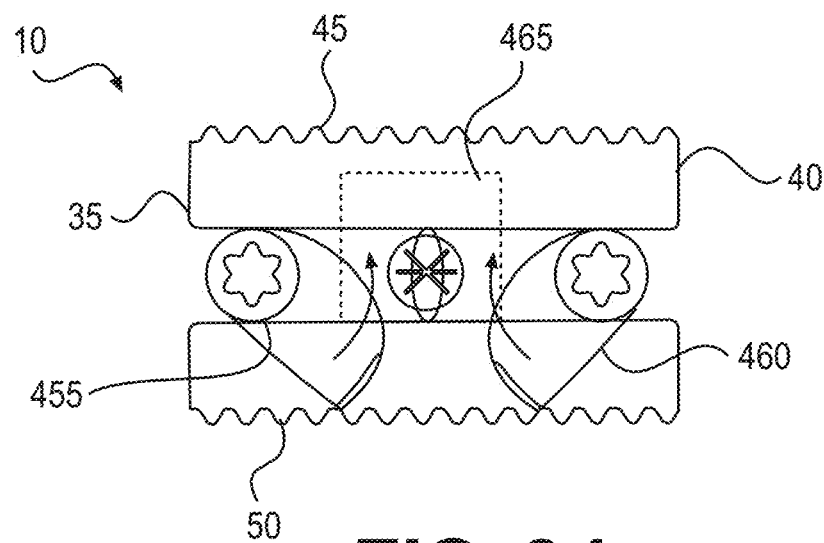
FIGS. 24 and 25 are end views of an expandable fusion device according to another embodiment of the present disclosure.
Figure 25:
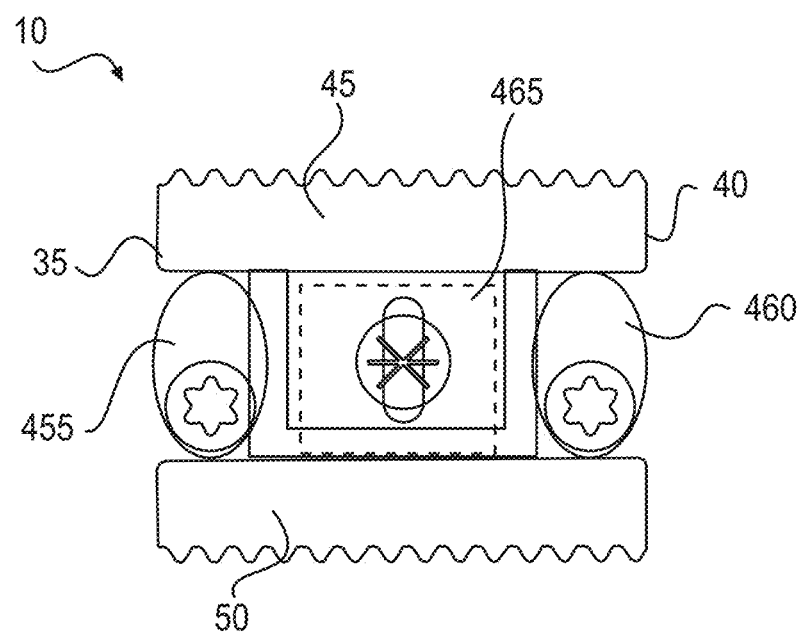

FIGS. 24 and 25 illustrate expandable fusion device 10 according to another embodiment. As illustrated, expandable fusion device 10 may comprise first endplate 45 and second endplate 50. A first cam member 455 and a second cam member 460 may be disposed between first endplate 45 and second endplate 50. First cam member 455 and second cam member 460 may each engage first endplate 45 and second endplate 50. First cam member 455 and second cam member 460 may each be rotatable. In some embodiments, first cam member 455 may be rotated to force first endplate 45 and second endplate 50 away from one another causing expansion on anterior side 35. In some embodiments, second cam member 460 may be rotated to force first endplate 45 and second endplate 50 away from one another causing expansion on posterior side 40. Expandable fusion device 10 may further comprise a linking plate 465 securing first endplate 45 to second endplate 50. FIG. 24 illustrates expandable fusion device 10 in a collapsed configuration. FIG. 25 illustrates expandable fusion device 10 in an expanded configuration after rotation of first cam member 455 and second cam member 460.

Figure 26:
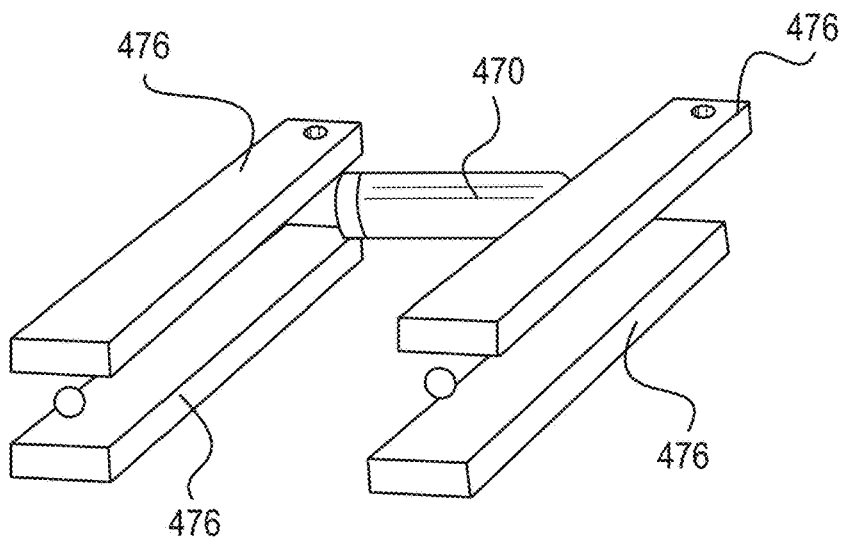
FIG. 26 is a perspective view of a translation member assembly in the form of translating bar according to another embodiment of the present disclosure.

FIG. 26 illustrates another expansion technique that may be used to activate expansion of an expandable fusion device 10 (e.g., shown on FIG. 1) in accordance with present embodiments. As illustrated, a central bar 470 may be disposed between endplate connectors 476, which may be coupled to corresponding endplates (e.g., first endplate 45 and second endplate 50 on FIG. 1). Central bar 470 may be moved to different locations between endplate connectors 476. Depending on positioning of central bar 470 between endplate connectors 476, there may be variable expansion of the endplates.

Figure 27:
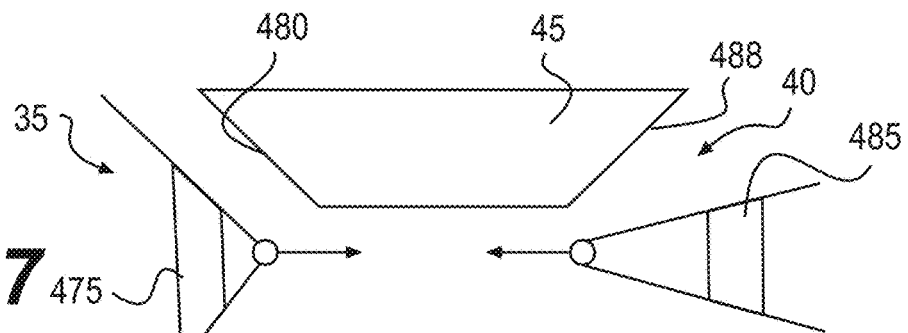
FIGS. 27-29 illustrate end views of a translation member assembly that incorporates side wedges according to another embodiment of the present disclosure.
Figure 28:
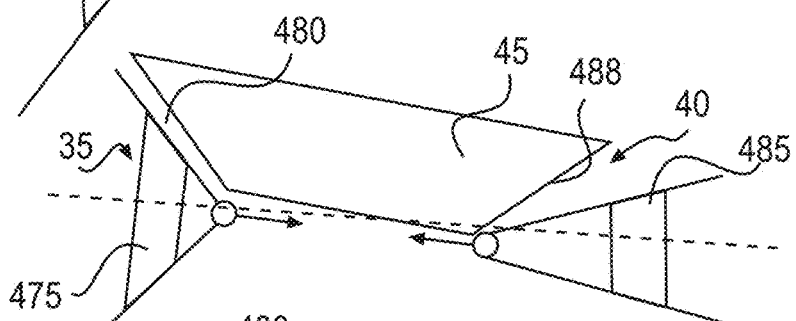
Figure 29:
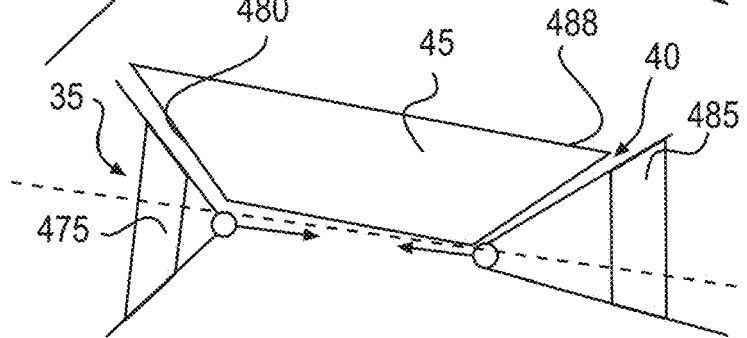
Figure 30:
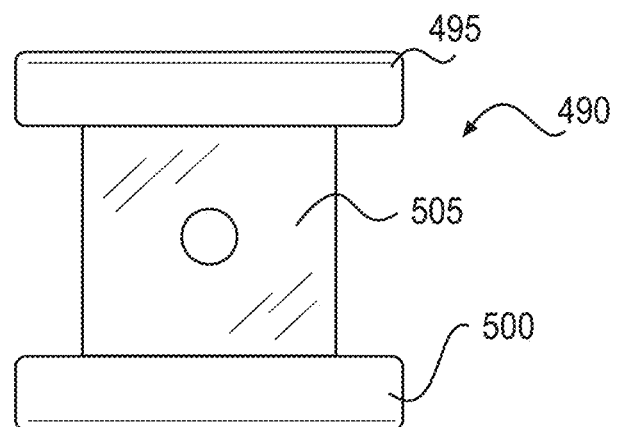
FIGS. 30-33 illustrate a corpectomy device according to another embodiment of the present disclosure.

FIGS. 27-29 illustrate another expansion technique that may be used to activate expansion of an expandable fusion device 10 (e.g., shown on FIG. 1) in accordance with present embodiments. For simplicity, only first endplate 45 is shown on FIGS. 27-29. Anterior wedge 475 may be positioned on anterior side 35 and may engage first endplate 45. For expansion on anterior side 35, anterior wedge 475 may be pushed into first endplate 45 from anterior side 35. As illustrated, anterior wedge 475 may engage a corresponding ramped surface 480 on first endplate 45 to push first endplate 45 outward causing expansion on anterior side 35. Posterior wedge 485 may be positioned on posterior side 40 and may also engage first endplate 45. For expansion on posterior side 40, posterior wedge 485 may be pushed into first endplate 45 from posterior side 40. As illustrated, posterior wedge 485 may engage a corresponding ramped surface 488 on first endplate 45 to push first endplate outward causing expansion on posterior side 40. In some embodiments, anterior wedge 475 and posterior wedge 485 may be pushed into first endplate 45 in a direction generally transverse to a longitudinal axis of the expandable fusion device.

Figures 31, 32, 33:
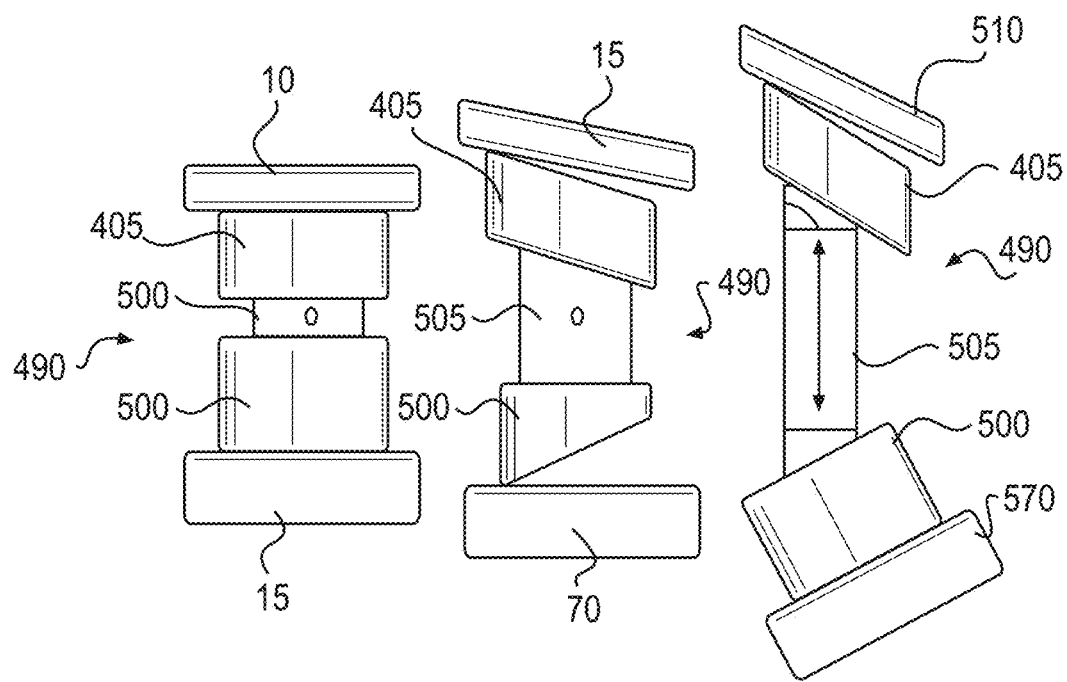

FIGS. 30-33 illustrate expansion of a corpectomy device 490 according to some embodiments. As illustrated on FIG. 30, corpectomy device 490 may comprise a first cutting endplate 495 and a second cutting endplate 500. First cutting endplate 495 and second cutting endplate 500 may be operable to cut away vertebral bodies. A cam member 505 may be disposed between first cutting endplate 495 and second cutting endplate 500. Rotation of cam member 505 may force first cutting endplate 495 and second cutting endplate 500 away from one another causing expansion of corpectomy device 490. FIG. 31 illustrates corpectomy device 490 disposed between adjacent vertebral bodies 15 and 20. Cam member 505 may be rotated to adjust the angel between the first cutting endplate 495 and second cutting endplate 500, as shown on FIG. 32. In some embodiments, corpectomy device 490 may be used to remove adjacent vertebral bodies 15 and 20 and then expanded to engage additional vertebral bodies 510 and 515, as shown on FIG. 33.

FIGS. 34 and 35 illustrate another expansion technique that may be used to activate expansion of an expandable fusion device 10 (e.g., shown on FIG. 1) in accordance with present embodiments. FIG. 34 is cross-sectional side view of an expandable fusion device 10 taken through anterior side 35 in accordance with present embodiments. As illustrated, on FIG. 35 an anterior ramped translation member 520 may be disposed between first endplate 45 and second endplate 50. Anterior ramped translation member 520 may be disposed on anterior side 35 (e.g., shown on FIG. 1) of expandable fusion device 10. Anterior ramped translation member 520 may comprise a plurality of ramped portions 525, which may engage corresponding ramped portions 530 in the first endplate 45 and second endplate 50. Anterior ramped translation member 520 may be moved such that ramped portions 525 in engage ramped portions 530 to cause first endplate 45 and second endplate 50 to move away from one another. FIG. 35 is a cross-sectional end view of an expandable fusion device 10 in accordance with present embodiments. Anterior ramped translation member 520 is shown between first endplate 45 and second endplate 50. A linkage assembly 535 may engage anterior ramped translation member 520. Linkage assembly 535 may comprise a central arm 540 that engages anterior ramped translation member 520 and extension arms 545. Extensions arms 545 may be engaged to first endplate 45 and second endplate 50 on posterior side 40 at pivot points 550 for anterior expansion. In some embodiments, linkage assembly 535 may be driven posteriorly to increase posterior height $H_p$. In some embodiments, first endplate 45 and second endplate 50 may comprise one or alternate pivot points 555. By setting extension arms 545 in alternative pivot points 555, for example, the relationship between anterior height $H_a$, posterior height $H_p$, and lordotic angle θ may be adjusted.

Figure 36:
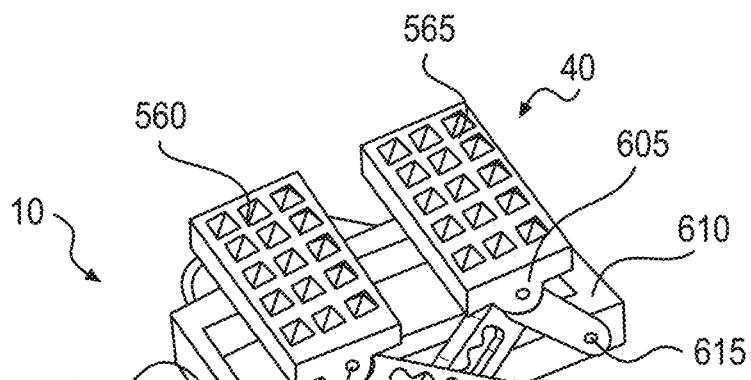
FIGS. 36 and 37 illustrate another technique for expansion of an expandable fusion device according to the present disclosure.
Figure 37:
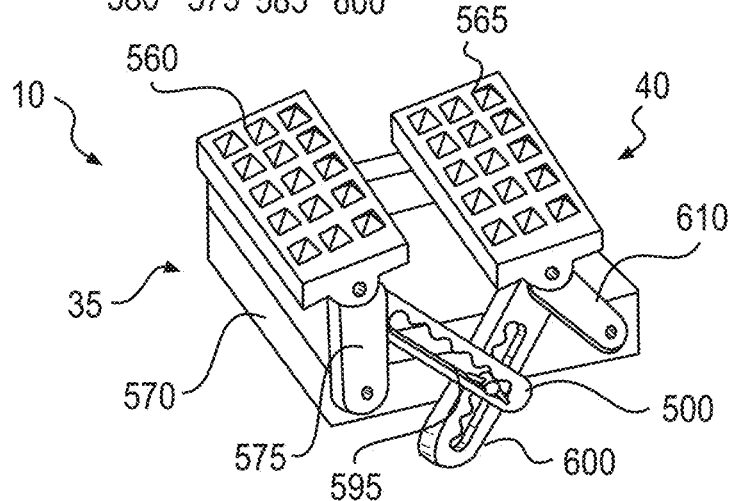

FIGS. 36 and 37 illustrate expandable fusion device 10 according to another embodiment. As illustrated, expandable fusion device 10 may comprise upper anterior endplate 560 and upper posterior endplate 565. For simplicity, the lower endplates are not shown in the embodiment illustrated on FIGS. 36 and 37. As illustrated, expandable fusion device 10 may further comprise frame 570. A first arm 575 may be coupled to upper anterior endplate 560 and frame 570. First arm 575 may pivot at connection point 580 with frame and also pivot at connection point 585 with upper anterior endplate 560. First rack lever 590 may also be pivotally coupled to upper anterior endplate 560 at connection point 585. First rack lever 590 and a second rack lever 600 may be pivotally coupled to frame 570 at a connection point 595. Second rack lever 600 may be pivotally coupled to upper posterior endplate 565 at connection point 605. A second arm 610 may be coupled to upper posterior endplate 565 at connection point 605 and may also be coupled to frame 570 at connection point 615. Second arm 610 may pivot at connection point 615 with frame and also pivot at connection point 605 with upper posterior endplate 565. For expansion on anterior side 35, a gear member (not shown) may engage first rack lever 590 and then be rotated, thus causing anterior side 35 to raise, as shown on FIG. 37. For expansion on posterior side 40, a gear member (not shown) may engage second rack lever 600 and then be rotated, thus causing posterior side 40 to raise.

Figure 38:
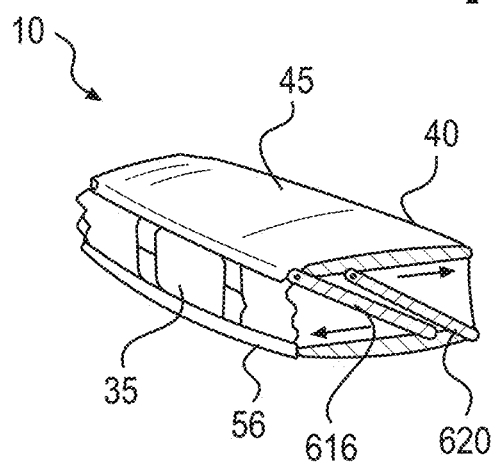
FIGS. 38 and 39 illustrate another technique for expansion of an expandable fusion device according to the present disclosure.
Figure 39:
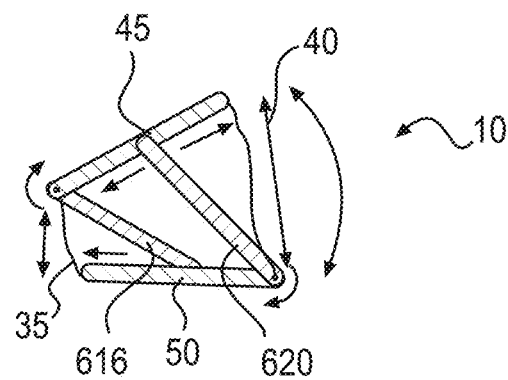
Figure 50:
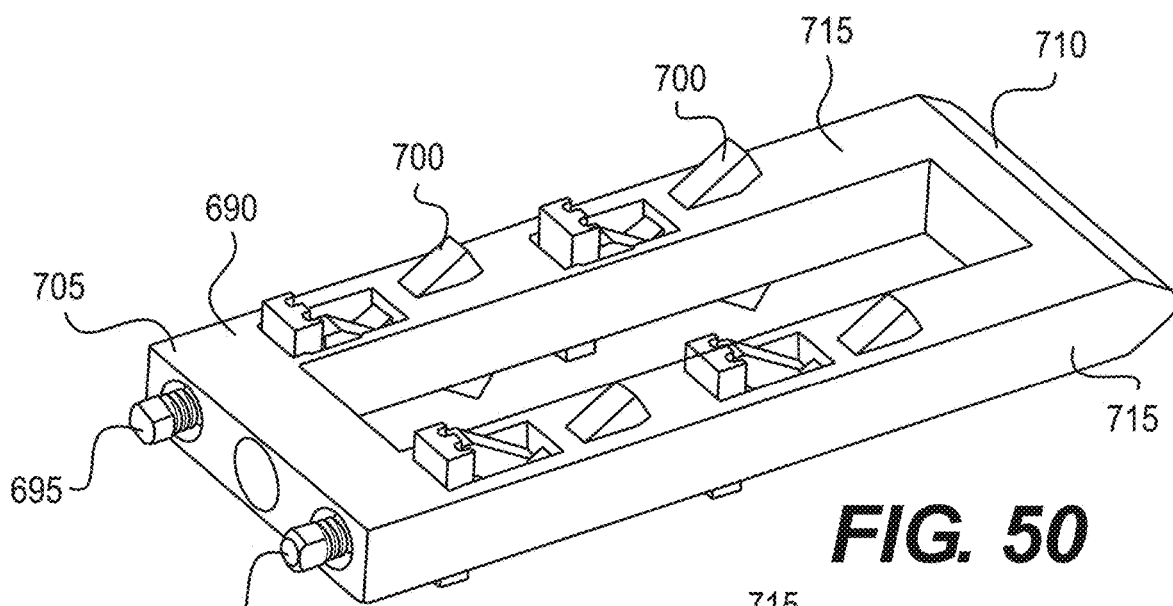
FIGS. 50-54 illustrate another technique for expansion of an expandable fusion device according to the present disclosure.

FIGS. 38 and 39 illustrate expandable fusion device 10 according to another embodiment. As illustrated, expandable fusion device 10 may comprise a first endplate 45 and a second endplate 50. A pair of internal arms 616 and 620 may be disposed between first endplate 45 and second endplate 50, wherein each of internal arms 616 and 620 engage the first endplate 45 and the second endplate 50. Internal arms 616 and 620 may be coupled to different endplates on opposite sides of the expandable fusion device 10. For example, internal arm 615 may be coupled to first endplate 45 on anterior side 35, while internal arm 620 may be coupled to second endplate 50 on posterior side 40. Rotation of the internal arms 616 and 620 about their respective connection points pushes the first endplate 45 and second endplate 50 apart, resulting in an increase in height. As each of the internal arms 616 and 620 is connected at a different side of the expandable fusion device 10, internal arms 616 and 620 may be independently rotated allowing for independent expansion of anterior side 35 and posterior side 40. Any of a variety of suitable techniques may be used for rotation of internal arms 616 and 620. By way of example, the internals arms 616 and 620 may be directly rotated at their respective connection points to the first endplate 45 and second endplate 50. Another rotation technique may include moving one of the internal arms 616 and 620 outward manually where it meets the endplate but is not connected to the endplate.

FIG. 40 illustrates expandable fusion device 10 according to another embodiment. In the illustrated embodiment, expandable fusion device 10 may comprise independently adjustable anterior and posterior endplates, such as upper anterior endplates 625 and upper posterior endplates 630. The endplates, such as upper anterior endplates 625 and upper posterior endplates 630, may have independent expansion mechanisms so facilitate independent expansion on anterior side 35 and posterior side 40. In some embodiments, expansion of upper anterior endplate 625 may be actuated by first actuation screw 75 and upper posterior endplate 630 may be actuated by second actuation screw 80.

FIGS. 41 to 45 illustrate expandable fusion device 10 according to another embodiment. The illustrated embodiment is similar to the embodiment of FIG. 40 except expansion may be facilitated through a single hole 635. FIG. 41 is a perspective view of the expandable fusion device 10 in accordance with present embodiments. FIG. 42 is a cross-sectional view of expandable fusion device 10 taken along plane 42 of FIG. 41, in accordance with present embodiments. As illustrated, expandable fusion device 10 may comprise a posterior ramped translation member 640 and an anterior ramped translation member 645. Implant driver 650, which may include an elongated shaft, may be disposed in hole 635, for example, with a threaded connection. Implant driver 650 may be moved forward or backwards to drive the translation member (e.g., posterior ramped translation member 640, anterior ramped translation member 645, or both) and, thus, push the endplates apart causing expansion. Distal end 655 of implant driver 650 may rotate to engage posterior ramped translation member 640, anterior ramped translation member 645, or both. FIG. 43 illustrates engagement of distal end 655 with posterior ramped translation member 640 in accordance with present embodiments. FIG. 44 illustrates engagement of distal end 655 with anterior ramped translation member 645 in accordance with present embodiments. FIG. 45 illustrates engagement of distal end 655 with both posterior ramped translation member 640 and anterior ramped translation member 645 in accordance with present embodiments.

FIG. 46 illustrates another technique for expansion of an expandable fusion device 10, for example, shown on FIG. 40 comprising a separately expandable anterior and posterior endplates arranged side by side. In the illustrated embodiment, a lordotic screw 660 may extend through rear plate 680 to engage posterior ramped translation member 640. As illustrated anterior ramped translation member 645 may comprise an extension 670 that is configured to engage a contact surface 665 of posterior ramped translation member 640. Lordotic angle $\theta$ may be set by rotating lordotic screw 660 to push posterior ramped translation member 640 and, thus, move contact surface 665 away from extension 670. Expansion screw 675 may be disposed through rear plate 680 to engage anterior ramped translation member 640. Expansion screw 675 may drive anterior ramped translation member 645 causing it to push against corresponding endplates (e.g., upper anterior endplates 625 and upper posterior endplates 630 on FIG. 40) moving them outward to thereby increase anterior height $H_a$. Anterior height $H_a$ may first be adjusted to a desired height greater than posterior height $H_p$ and then extension 670 may engage contact surface 665 such that anterior ramped translation member 645 pushed posterior ramped translation member 640 causing posterior ramped translation member 640 to push against corresponding endplates (e.g., upper anterior endplates 625 and upper posterior endplates 630 on FIG. 40) moving them outward to thereby also increase posterior height $H_p$. In some embodiments (not illustrated), the expandable fusion device 10 may first rock into a desired lordosis and then utilize ramps to expand the expandable fusion device 10.

FIGS. 47-49 illustrate another technique for expansion of an expandable fusion device 10, for example, shown on FIG. 1. In the illustrated embodiment, a ramped translation member 685 may be disposed between first endplate 45 and second endplate 50. Ramped translation member 685 may be in the general shape of spheroid, which may be oblate or prolate, for example. Ramped translation member 685 may be driven between the first endplate 45 and second endplate 50 to drive them apart to increase height. Lordosis may be achieved passively, in some embodiments, by allowing the first endplate 45 and/or the second endplate 50 to rock on the ramped translation member 685, as seen on FIG. 49. The first endplate 45 and second endplate 50 may contour to the lordosis of the disc space.

Figure 51:
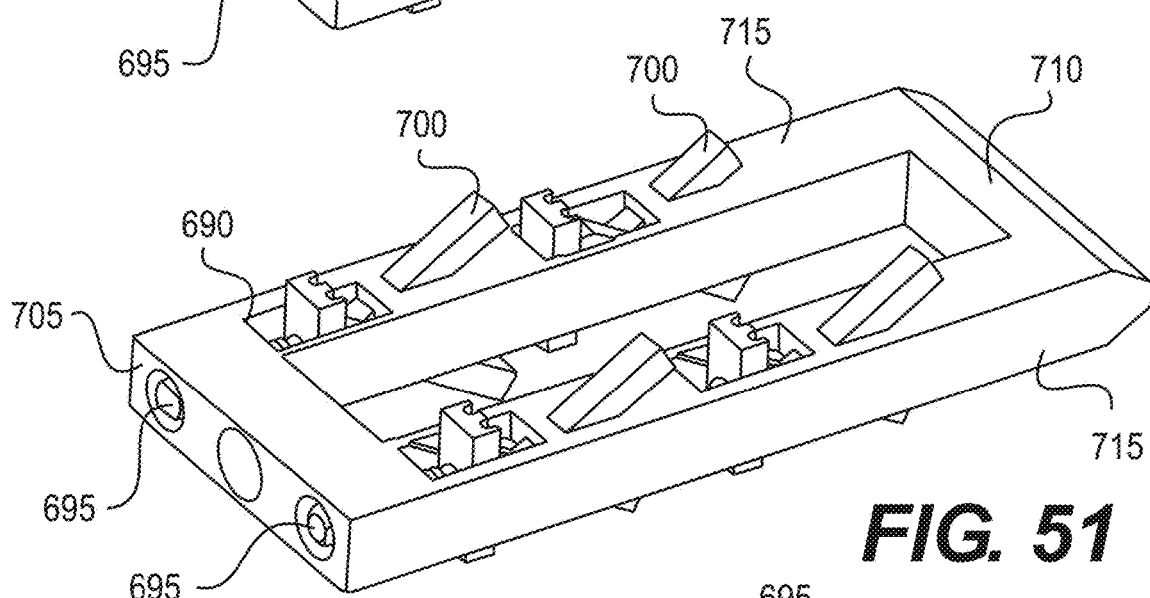
Figure 52:
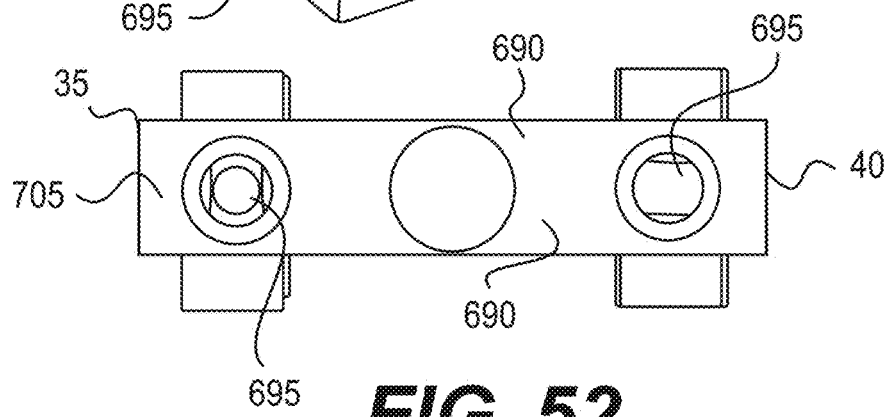
Figure 53:
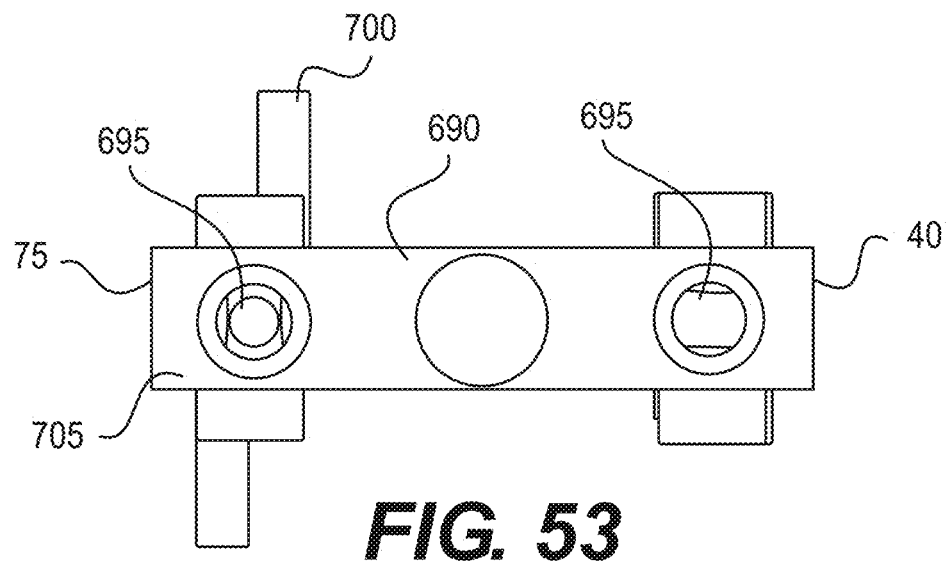
Figure 54:
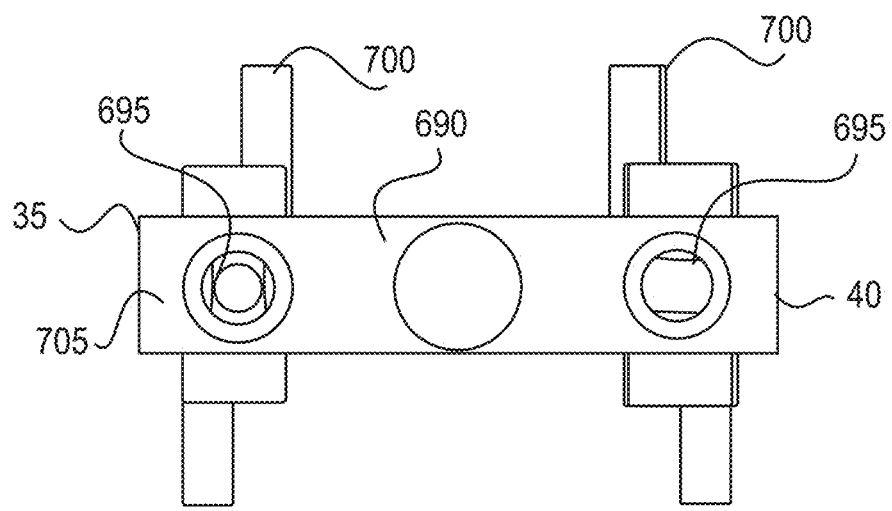

FIGS. 50-54 illustrate another technique for expansion of an expandable fusion device 10, for example, shown on FIG. 1. In the illustrated embodiment, an actuation frame 690 may comprise actuation screws 695 that drive ramps 700 disposed in the actuation frame 690. As illustrated, actuation frame 690 may comprise a proximal end 705 and a distal end 710, which may be tapered to facilitate insertion into the disc space, for example. Lateral sides 715 may couple the proximal end 705 and distal end 710. Ramps 700 may be disposed in lateral sides. Actuation screws 695 may be disposed in proximal end 705. As illustrated on FIG. 50, the ramps 700 may be at least partially retracted into actuation frame 690. Rotation of actuation screws 695 may extend ramps 700 from actuation frame 690, as seen in FIG. 51. FIGS. 52-54 are end views showing independent expansion of ramps on anterior side 35 and posterior side 40. FIG. 52 illustrates ramps 700 at least partially retracted in actuation frame 690. Actuation screw 695 on anterior side 35 may be rotated to cause ramps 700 on anterior side 35 to extend from actuation frame 690, as seen on FIG. 53. While not shown ramps 700 on anterior side 35 may engage endplates (e.g., first endplate 45, second endplate 50 on FIG. 2) to cause an increase in anterior height $H_a$. Actuation screw 695 on anterior side 35 may be rotated to cause ramps 700 on anterior side 35 to extend from actuation frame 690, as seen on FIG. 54. While not shown ramps 700 on anterior side 35 may engage endplates (e.g., first endplate 45, second endplate 50 on FIG. 2) to cause an increase in posterior height $H_p$.

FIGS. 55A-62B illustrate an exemplary embodiment consistent with the principles of the present disclosure. With reference now to FIG. 55A-C, an exemplary embodiment of an expandable fusion device 5500 is shown. Expandable fusion device 5500 may include a first endplate 5502, a second endplate 5504, and a translation member assembly 5506. Translation member assembly 5506 may further include anterior front ramp 5508, anterior back ramp 5510, posterior front ramp 5512, and posterior back ramp 5514. Device 5500 may also include joists 5516, 5518, 5520, and 5522. While reference to ramps 5508, 5510, 5512, and 5514 has been made according to the relative location within a patient after implantation, it should be noted that expandable fusion device 5500 may be implanted in a different orientation (for example, in a position upside down from the position as illustrated) thereby changing the relative anterior and posterior positions after implantation. Therefore, the position of ramps inside a patient is not limited and can be applicable to both anterior and posterior positions.

FIGS. 55A-55D and FIGS. 56A-D show device 5500 in different states of expansion and angled arrangements. FIGS. 55A and 56A illustrate device 5500 in a state of compression, which may be the state of implant upon initial insertion into adjacent vertebral bodies within a patient. This state of compression may be at a height of 7 mm but may also be other heights depending upon the particular circumstances of the surgical procedure and/or the target vertebral bodies. FIGS. 55B and 56B show device 5500 in a state of partial expansion wherein the first posterior ramp 5512 and second posterior ramp 5514 are moved by translation member 5506 in order to expand first endplate 5502 and second endplate 5504 on the posterior side, while keeping the anterior side in a compressed position or a position that is not as expanded as the posterior side, to create the shown angled arrangement of device 5500. FIGS. 55C and 56C show device 5500 in another angled arrangement, wherein translation member 5506 moves first anterior ramp 5508 and second anterior ramp 5510 in a manner resulting in first endplate 5502 and second endplate 5504 to expand on the anterior side while keeping the posterior side unexpanded or less expanded than the anterior side. FIG. 56C additionally illustrates joists 5520 and 5522 which are on the opposite side of joists 5516 and 5518. In FIG. 55D, device 5505 is shown in a state of full expansion wherein both the anterior and posterior sides are expanded by translation member 5506 by moving ramps 5508, 5510, 5512, and 5514. As shown in FIGS. 55A-56D, expansion device 5500 may be expanded to a desired posterior height and lordotic angle independent of each other as translation member 5506 may independently translate the anterior ramps 5508, 5510 (which move joists 5516 and 5518) and/or translate the posterior ramps 5512 and 5514 (which move joists 5520 and 5522).

FIGS. 57A and 57B illustrate device 5500 in a state of lordotic expansion wherein an anterior side 5524 of device 5500 is expanded while a posterior side 5526 remains in a compressed configuration. FIG. 57A illustrates device 5500 from the perspective of anterior front ramp 5508 and posterior front ramp 5512, which may be the end that is initially inserted into adjacent vertebral bodies. FIG. 57B illustrates device 5500 from the perspective of anterior back ramp 5510 and posterior back ramp 5512, which may be the end accessible to a surgeon after implantation of device 5500. In addition to elements that have already been explained, FIG. 57A illustrates front bores 5528 and 5530 and graft window 5540. FIG. 57B illustrates back bores 5532 and 5534, internal posterior bore 5536, and graft window 5540. In operation, device 5500 would be inserted (in a compressed state such as FIG. 55A) into a space between adjacent vertebral bodies with front ramps 5508 and 5512 being the leading end. After insertion, it may be determined that expansion of the anterior side of device 5500 is appropriate. This may be effected by inserting a tool into back bore 5532 and engaging a screw (not shown) disposed in translation member 5506 at a location that causes anterior front ramp 5508 to move closer to anterior back ramp 5510. This in turn causes joists 5516, 5518 to move along translation member 5506 to expand the anterior side 5524 of the device 5505 by separating first endplate 5502 and the second endplate 5504 from a compressed position. Once a desired position is reached, the screw is locked in place thereby securing the position of the endplates in the desired orientation. Because back bores 5532 and 5534 are open, graft material may be delivered to device 5500 through one or both of bores 5532 and 5534 into translation member 5506 which may then flow out if graft window 5540. The creates a manner in which to backfill device 5500 with graft material after implantation. The operation of translation member 5506, joists 5516, 5518, 5520, 5526, endplates 5502 and 5504 are explained in greater detail below.

FIGS. 58A-58B illustrate an exemplary embodiment of translation member 5506 that may be used in expansion fusion device 5500. In addition to components previously described, translation member 5506 may include anterior translation bar 5542, posterior translation bar 5544, ramps 5546, posterior translation component 5548, anterior translation component 5550, posterior screw or actuation member 5552, anterior screw or actuation member 5554, anterior interior bore 5556. In an exemplary operation, anterior translation bar 5542 may be connected to joists 5516 and 5518, which in turn may be connected to an anterior side of first endplate 5502 and second endplate 5504.

Movement of device 5500 in order to expand the endplates 5502 and/or 5504 may be done by a mechanical mechanism that allows for the front and back ramps to slide towards each other and lock in position once a desired expansion has been achieved. For example, in order to expand on the anterior side, anterior translation bar 5542 may be engaged by inserting a tool through back bore 5536 to engage screw 5554 disposed in anterior internal bore 5556 and connected to front bore 5528. By turning screw 5554, anterior front ramp 5508 may be moved closer to anterior translation component 5550. Joists 5516 and 5518 that are connected to the anterior translation bar 5542 slide along ramps 5546 on the anterior side via corresponding ramps disposed on joints 5516 and 5518 to expand endplates 5502 and 5504 from the compressed position. The orientation may be locked once the desired expansion has been achieved.

FIG. 58B illustrates a top view of translation member 5506, wherein posterior translation bar 5544 is moved closer to posterior front ramp 5512. This would have the effect of moving corresponding joists 5520, 5522 to expand the posterior side of endplates 5502 and 5504.

Figure 59:
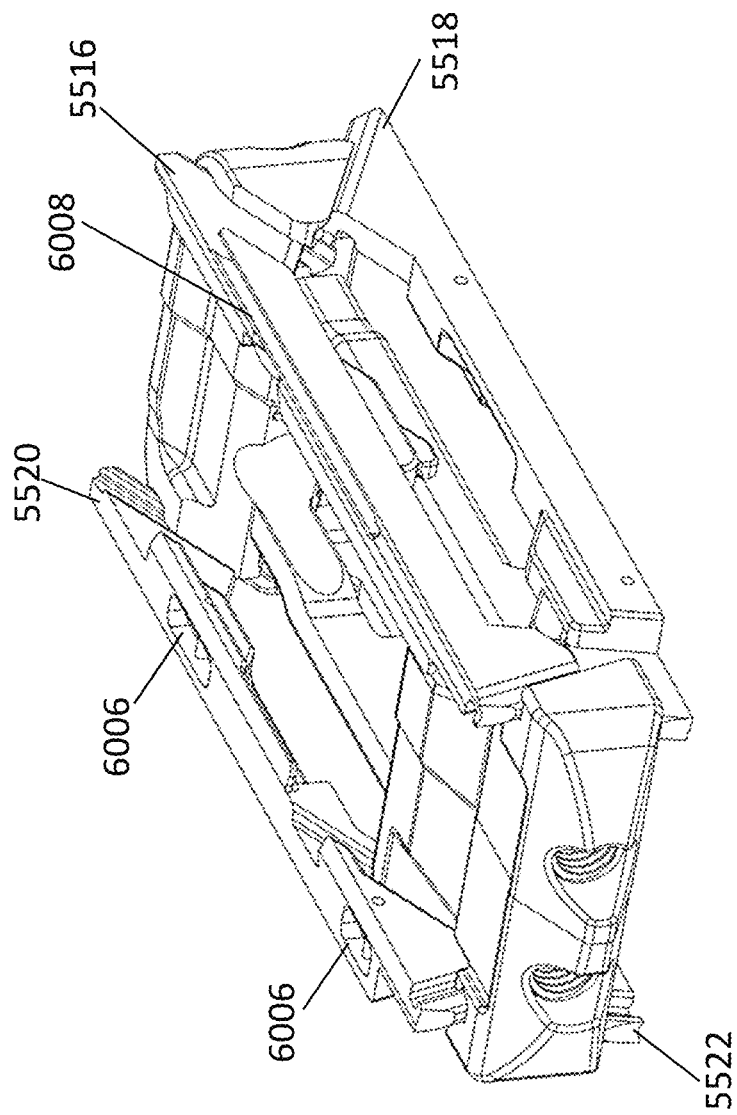
FIG. 59 illustrates a perspective view of an exemplary translation member and joists for an expandable fusion device according to an embodiment of the present disclosure.
Figure 60B:
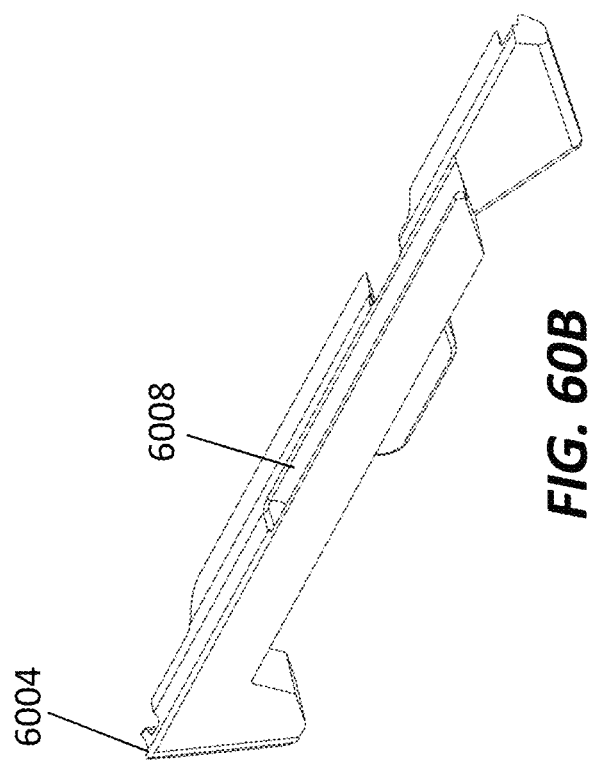
FIGS. 60A and 60B illustrate perspective views of two exemplary embodiments of a joist for an expandable fusion device.
Figure 60A:
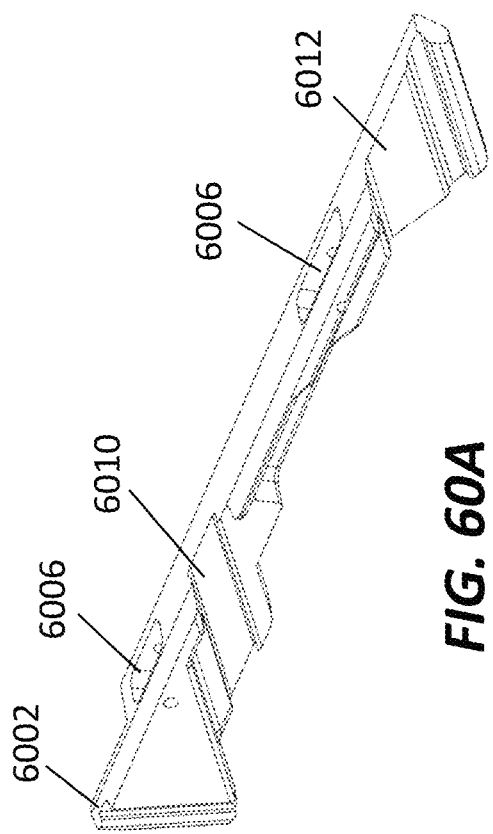

Referring to FIGS. 59-61B, FIG. 59 illustrates an exemplary embodiment of translation member 5506 connected to joists 5516, 5518, 5520, and 5522. Due to the perspective of FIG. 59, joist 5522 is not shown. FIG. 60 shows two exemplary types of joists. FIG. 61A-61B show an exemplary embodiment of either endplate 5502 or 5504 and the manner it may engage the two types of joists illustrated in FIG. 60.

Joists 5516, 5518, 5520, and 5522 may contain separate components configured to engage endplates 5502, 5504 using different types of attachment mechanisms and may contain ramps that engage translation member 5506. For example, FIG. 60 illustrates a first type of joist 6002 and a second type of joist 6004. Joist 6002 may contain pockets 6006 and joist 6004 may contain a cylindrical bore 6008. The joists may also contain ramps 6010 configured to engage corresponding ramps 5546. Previously mentioned joists 5516, 5518, 5520, and 5520 may be either type of joist.

In exemplary embodiments, the joists may be disposed such that a top side of device 5500 contains one type of joist (for example, joist 6002) on one side of the device (either anterior or posterior) and the other type of joist (for example, joist 6004) on the other side of the device. As shown in FIG. 59, joist 5516 may have cylindrical bore 6008 and joist 5520 may have pockets 6006. Pockets 6006 may be configured to engage tabs 6102 disposed on an underside of one of the endplates. For example, FIG. 61A shows the underside of endplate 5502 with tabs 6102 disposed on one side and a cylindrical stem 6104 disposed on the other side that is configured to engage cylindrical bore 6008. As shown in FIG. 61B, endplate 5502 may be configured to be disposed on joists 5516 and 5520 using this type of engagement. Fully assembled, device 5500 would appear as illustrated in FIGS. 55A-55D.

Cylindrical stem 6104 and cylindrical bore 6008 may provide a set point from each of endplates 5502, 5504 may pivot. Tabs 6102 may be configured such that they pivot inside the respective pockets 6006 and/or slide towards the opposing side of device 5500. This migration, however slight, may allow endplates 5502 and 5504 to articulate while device 5500 is at a fixed width.

Figure 62B:
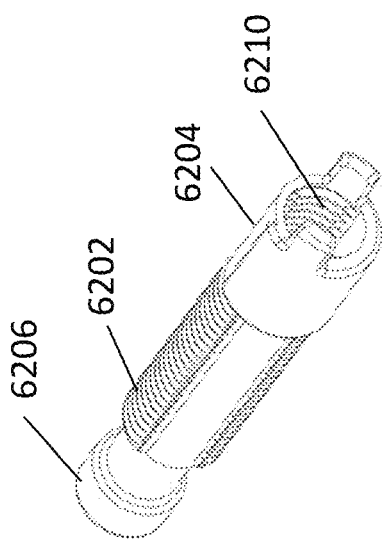
FIGS. 62A-62B illustrate perspective views of an exemplary locking stem for an expandable fusion device according to an embodiment of the present disclosure.
Figure 62A:
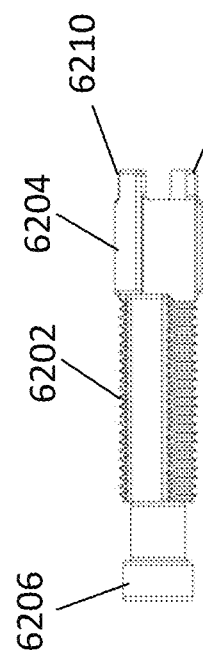
Figure 62C:
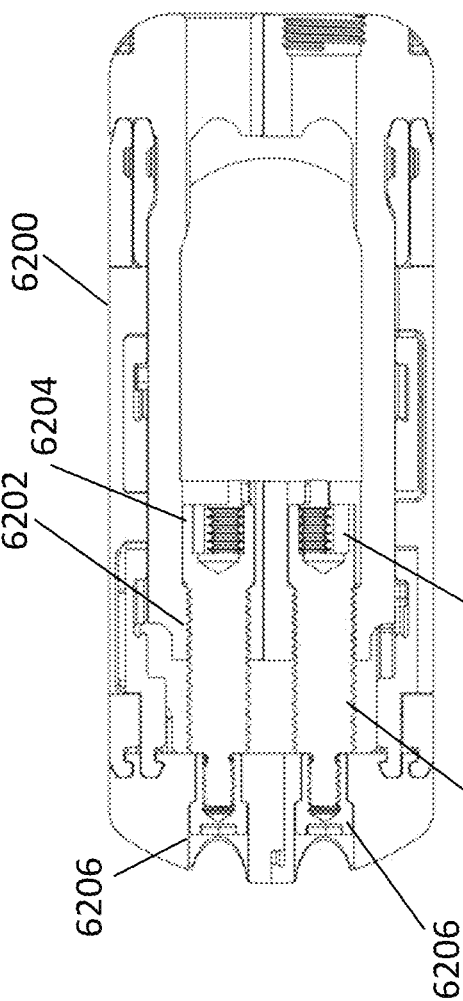
FIG. 62C illustrates a perspective view of an exemplary translation member for an expandable fusion device according to an embodiment of the present disclosure.
Figure 63:
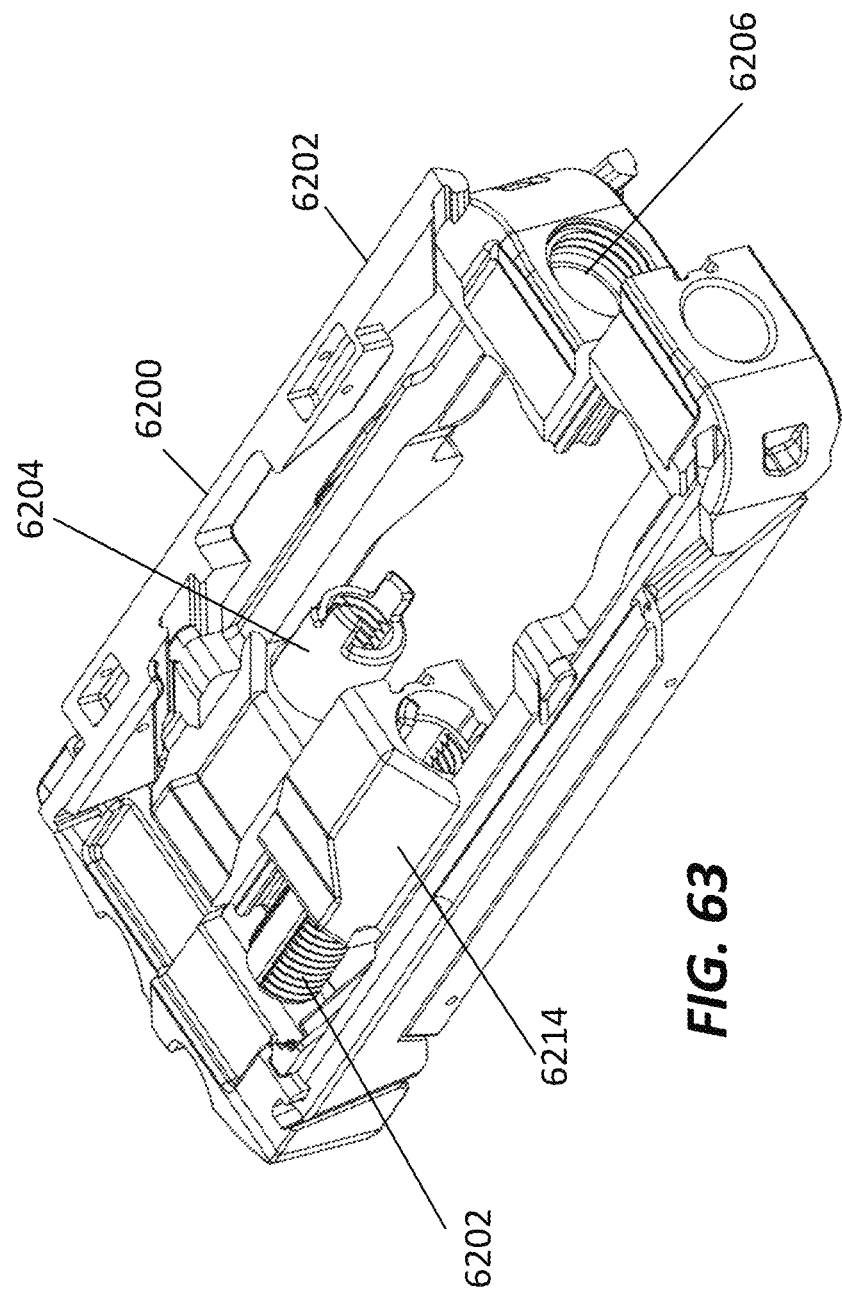
FIG. 63 illustrates a perspective view of an exemplary translation member for an expandable fusion device according to an embodiment of the present disclosure.

FIGS. 62A-63 show an exemplary embodiment of a translation member 6200 consistent with the principles of the present disclosure. Translation member 6200 is similar to other translation members discussed herein. Translation member 6200 may contain a locking stem 6202 which may be disposed therein. Locking stem 6202 may comprise internal teeth 6208 and counter-torque tabs 6210.

Teeth 6208 and tabs 6210 may engage a tool that is inserted into opening 6206 of translation member 6200 in order to provide a rigid connection between locking stem 6202 and the tool. The tool may then be used to manipulate translation member 6200 to ultimately expand a fusion device containing translation member 6200. In operation, while the tool is engaged with locking stem 6202 and is manually drawn towards opening 6206, the fusion device may expand due to endplates secured to translation member 6200 as otherwise provided herein, for example, using joists discussed above. When moved in a direction away from opening 6206, the fusion device may move to a more compressed state. In order to fix the position of the desired expansion or compression, locking stem 6202 may be locked by rotating locking stem 6202, for example, by rotating the locking stem by 90°. Upon this rotation, external teeth 6212 of locking stem 6202 may engage with internal teeth inside internal ramps 6214 of translation member 6200 (shown in FIG. 63) to lock device 6200 in a desired orientation.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed, the invention covers all combinations of all those embodiments.

What is claimed is:

1. A method of installing an expandable fusion device, said method comprising:
    preparing an intervertebral disc space by at least partially removing an intervertebral disc between adjacent vertebrae;
    creating an exposed end surface on each of the adjacent vertebrae;
    inserting an endoscopic tube into the disc space; and
    introducing the expandable fusion device into the intervertebral disc space via the endoscopic tube,
    wherein the expandable fusion device includes:
        a first endplate;
        a second endplate;
        a first joist and a second joist connected to the first endplate;
        a third joist and a fourth joist connected to the second endplate;
        a translation member assembly in engagement with the first joist, second joist, third joist, and fourth joist;
        a first actuation member in engagement with the translation member assembly, wherein the first actuation member is configured to move the first joist and the third joist such that the first endplate and the second endplate move in a direction away from the translation member assembly on a first side of the expandable fusion device; and
        a second actuation member in engagement with the translation member assembly, wherein the second actuation member is configured to move the second joist and the fourth joist such that the first endplate and the second endplate move in a direction away from the translation member assembly on a second side of the expandable fusion device,
    wherein the first actuation member and the second actuation member are parallel and operate independently of one another, and
    wherein the first joist includes a pocket configured to receive a tab disposed on the first endplate.

2. The expandable fusion device of claim 1, wherein the first side is an anterior side, and wherein the second side is a posterior side.

3. The method of claim 1, further comprising a first anterior ramp frame and a second anterior ramp frame on the first side of the expandable fusion device.

4. The method of claim 1, further comprising a first posterior ramp frame and a second posterior ramp frame on the second side of the expandable fusion device.

5. The method of claim 1, wherein the translation member further comprises an anterior translation bar and a posterior translation bar.

6. The method of claim 5, wherein the anterior translation bar engages the first joist and third joist.

7. The method of claim 6, wherein the posterior translation bar engages the second joist and the fourth joist.

8. The method of claim 1, wherein the expandable fusion device contains a front side and a back side, wherein the front side is configured to lead the fusion device into an intervertebral space, and the backside contains one or more openings to receive a tool to engage the first actuation member and second actuation member, and wherein the one or more openings are configured to receive graft material.

9. The method of claim 1, wherein the translation member further comprises an anterior translation component containing an anterior bore, wherein the first actuation member is disposed within the anterior bore.

10. The method of claim 9, wherein the translation member further comprises a posterior translation component containing a posterior bore, wherein the second actuation member is disposed within the posterior bore.

11. A method of installing an expandable fusion device, said method comprising:
preparing an intervertebral disc space by at least partially removing an intervertebral disc between adjacent vertebrae;
creating an exposed end surface on each of the adjacent vertebrae;
inserting an endoscopic tube into the disc space; and
introducing the expandable fusion device into the intervertebral disc space via the endoscopic tube,
wherein the expandable fusion device includes:
a first endplate;
a second endplate; and
a translation member disposed at least partially between the first endplate and the second endplate, wherein the translation member assembly includes:
an anterior translation component disposed on an anterior side of the expandable fusion device, wherein the anterior translation portion comprises an anterior bore; and
a posterior translation component disposed on a posterior side of the expandable fusion device, wherein the posterior translation portion comprises a posterior bore,
wherein the translation member is configured to expand the fusion device on an anterior side by moving an anterior side of the first endplate and an anterior side of the second endplate,
wherein the translation member is configured to expand the fusion device on a posterior side by moving a posterior side of the first endplate and a posterior side of the second endplate;
wherein the first endplate is engaged with the translation member via a first joist and a second joist,
wherein the second endplate is engaged with the translation member via a third joist and a fourth joist,
wherein a first actuation member and a second actuation member are parallel and operate independently of one another, and
wherein the first joist includes a pocket configured to receive a tab disposed on the first endplate.

12. The method of claim 11, wherein the second joist comprises a cylindrical bore configured to receive a cylindrical stem disposed on the first endplate.

13. The method of claim 12, wherein the third joist comprises a pocket configured to receive a tab disposed on the second endplate, and wherein the fourth joist comprises a cylindrical bore configured to receive a cylindrical stem disposed on the second endplate.

14. The method of claim 11, further comprising a first and second anterior ramp frames on the anterior side and further comprising first and second posterior ramp frames on the posterior side.

15. The method of claim 11, wherein the translation member further comprises an anterior translation bar and a posterior translation bar.

16. The method of claim 15, wherein the anterior translation bar engages the first joist and third joist.

17. The method of claim 16, wherein the posterior translation bar engages the second joist and the fourth joist.

18. The method of claim 11, wherein the first actuation member is disposed within the anterior bore.

19. The method of claim 18, wherein the second actuation member is disposed within the posterior bore.

20. A method of installing an expandable fusion device, said method comprising:
preparing an intervertebral disc space by at least partially removing an intervertebral disc between adjacent vertebrae;
creating an exposed end surface on each of the adjacent vertebrae;
inserting an endoscopic tube into the disc space; and
introducing the expandable fusion device into the intervertebral disc space via the endoscopic tube,
wherein the expandable fusion device includes:
a first endplate;
a second endplate;
a first joist and a second joist connected to the first endplate;
a third joist and a fourth joist connected to the second endplate;
a translation member assembly in engagement with the first joist, second joist, third joist, and fourth joist;
a first actuation member in engagement with the translation member assembly, wherein the first actuation member is configured to move the first joist and the third joist such that the first endplate and the second endplate move in a direction away from the translation member assembly on a first side of the expandable fusion device; and
a second actuation member in engagement with the translation member assembly, wherein the second actuation member is configured to move the second joist and the fourth joist such that the first endplate and the second endplate move in a direction away from the translation member assembly on a second side of the expandable fusion device
wherein the expandable fusion contains one or more openings to receive a tool to engage the translation member, and wherein the one or more openings are configured to receive graft material,
wherein the first actuation member and the second actuation member are parallel and operate independently of one another, and wherein the first joist includes a pocket configured to receive a tab disposed on the first endplate.

\* \* \* \* \*